(12) United States Patent
Dye

(10) Patent No.: US 10,835,365 B2
(45) Date of Patent: Nov. 17, 2020

(54) VESSEL DISSECTION AND HARVESTING APPARATUS, SYSTEMS AND METHODS

(71) Applicant: Mayo Foundation for Medical Education and Research, Rochester, MN (US)

(72) Inventor: Kenneth R. Dye, Neptune Beach, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 317 days.

(21) Appl. No.: 15/806,557

(22) Filed: Nov. 8, 2017

(65) Prior Publication Data

US 2018/0064528 A1 Mar. 8, 2018

Related U.S. Application Data

(62) Division of application No. 13/996,645, filed as application No. PCT/US2011/067139 on Dec. 23, 2011, now Pat. No. 9,833,308.

(Continued)

(51) Int. Cl.
*A61B 17/00* (2006.01)
*A61F 2/06* (2013.01)
(Continued)

(52) U.S. Cl.
CPC .......... *A61F 2/062* (2013.01); *A61B 5/02152* (2013.01); *A61B 17/00008* (2013.01); *A61B 17/00234* (2013.01); *A61B 17/0218* (2013.01); *A61B 17/320016* (2013.01); *A61B 17/22031* (2013.01); *A61B 17/29* (2013.01); *A61B 17/3474* (2013.01); *A61B 2017/320064* (2013.01); *A61B 2017/3445* (2013.01); *A61B 2090/064* (2016.02); *A61B 2218/002* (2013.01); *Y10T 29/49826* (2015.01)

(58) Field of Classification Search
CPC .......... A61B 17/00008; A61B 17/0483; A61B 17/22031; A61B 17/221; A61B 17/26; A61B 17/28; A61B 17/29; A61B 17/32; A61B 17/320016; A61B 17/3205; A61B 17/32056; A61B 17/00353; A61B 17/00358; A61B 17/00969; A61B 17/1125; A61B 17/320064; A61B 17/4233; A61B 10/06

See application file for complete search history.

(56) References Cited

U.S. PATENT DOCUMENTS 4,754,752 A 7/1988 Ginsburg et al.
5,800,408 A 9/1998 Strauss et al.
(Continued)

OTHER PUBLICATIONS

International Search Report and Written Opinion, dated Jun. 26, 2012, International Application No. PCT/US2011/067139.
(Continued)

*Primary Examiner* — Darwin P Erezo
*Assistant Examiner* — Christian D Knauss
(74) *Attorney, Agent, or Firm* — Mueting Raasch Group

(57) ABSTRACT

Apparatus, systems, and methods for endoscopic dissection of blood vessels and control over cavity pressure within an endoscopic procedure are described herein. Apparatus, systems, and methods for harvesting of blood vessels are also described herein.

23 Claims, 14 Drawing Sheets

Related U.S. Application Data

(60) Provisional application No. 61/426,932, filed on Dec. 23, 2010, provisional application No. 61/467,482, filed on Mar. 25, 2011.

(51) Int. Cl.

| | | |
|---|---|---|
| *A61B 5/0215* | (2006.01) | |
| *A61B 17/02* | (2006.01) | |
| *A61B 17/32* | (2006.01) | |
| *A61B 17/22* | (2006.01) | |
| *A61B 17/29* | (2006.01) | |
| *A61B 17/34* | (2006.01) | |
| *A61B 90/00* | (2016.01) | |

(56) References Cited

U.S. PATENT DOCUMENTS

| | | | |
|---|---|---|---|
| 5,891,140 A | | 4/1999 | Ginn et al. |
| 5,893,848 A | | 4/1999 | Negus et al. |
| 5,902,315 A | | 5/1999 | DuBois |
| 5,913,818 A | | 6/1999 | Co et al. |
| 6,036,713 A | | 3/2000 | Kieturakis |
| 6,152,936 A | * | 11/2000 | Christy .............. A61B 17/0483 606/139 |
| 6,660,016 B2 | | 12/2003 | Lindsay |
| 6,749,572 B2 | | 6/2004 | Edwardsen et al. |
| 6,749,609 B1 | | 6/2004 | Lunsford et al. |
| 7,556,633 B2 | | 7/2009 | Lindsay |
| 7,651,503 B1 | * | 1/2010 | Coe ................ A61B 17/320016 606/108 |
| 2002/0128546 A1 | | 9/2002 | Silver |
| 2003/0130675 A1 | * | 7/2003 | Kasahara ......... A61B 17/00008 606/159 |
| 2005/0010242 A1 | | 1/2005 | Lindsay |
| 2005/0192613 A1 | * | 9/2005 | Lindsay ........... A61B 17/00008 606/190 |
| 2005/0260176 A1 | | 11/2005 | Ayares et al. |
| 2006/0079740 A1 | | 4/2006 | Silver et al. |
| 2006/0224110 A1 | | 10/2006 | Scott et al. |
| 2008/0154297 A1 | | 6/2008 | Lee et al. |
| 2008/0176271 A1 | | 7/2008 | Silver et al. |
| 2008/0306335 A1 | | 12/2008 | Lau et al. |
| 2009/0023986 A1 | | 1/2009 | Stewart et al. |
| 2009/0024156 A1 | | 1/2009 | Chin |
| 2010/0114304 A1 | | 5/2010 | Craig |
| 2011/0046624 A1 | * | 2/2011 | Lin ................. A61B 17/00008 606/51 |
| 2014/0323800 A1 | | 10/2014 | Dye |

OTHER PUBLICATIONS

International Preliminary Report on Patentability, mailed Jul. 4, 2013, International Application No. PCT US2011/067139.

\* cited by examiner

VESSEL DISSECTION AND HARVESTING APPARATUS, SYSTEMS AND METHODS

RELATED APPLICATIONS

The present application is a divisional of U.S. patent application Ser. No. 13/996,645 filed Sep. 30, 2013, which is a U.S. National Stage Application of International Application No. PCT/US2011/067139, titled VESSEL DISSECTION AND HARVESTING APPARATUS, SYSTEMS AND METHODS, filed on Dec. 23, 2011, published in the English language on Jun. 28, 2012 as International Publication No. WO 2012/088501 A2, which claims the benefit under 35 U.S.C. § 119(e) of U.S. Provisional Patent Application No. 61/426,932, filed on Dec. 23, 2010, titled VESSEL DISSECTION APPARATUS, SYSTEMS AND METHODS, and of U.S. Provisional Patent Application No. 61/467,482, filed on Mar. 25, 2011, titled VESSEL HARVESTING APPARATUS, SYSTEMS AND METHODS, each of which are hereby incorporated by reference in their entirety.

Apparatus, systems, and methods for endoscopic dissection of blood vessels and control over cavity pressure within an endoscopic procedure are described herein. Apparatus, systems, and methods for endoscopic harvesting of blood vessels are also described herein.

Endoscopic vessel harvesting (EVH) involves the use of a variety of equipment that is also used in general laparoscopic and thoracoscopic surgery. This equipment may include a video tower, carbon dioxide insufflation tubing, camera attachments, cautery cords, and endoscopes. The procedure is typically accomplished in a two-phase approach. The first phase involves the dissection, or freeing of the blood vessel from the surrounding subcutaneous tissue with a specialized dissection device.

Blood vessel dissection devices are typically introduced into an access incision either directly or through a device guide (e.g., a trocar), which is placed overlying the vessel. The vessel is then visualized or mapped endoscopically, and the dissection device is advanced along the anterior, posterior and lateral borders of the vessel. The vessel is preferably freed circumferentially from surround tissue and structures including all lateral side branches that exist along the course of the vessel. Carbon dioxide flows through the device or trocar into the dissection cavity to maintain an adequate working space around the vessel.

SUMMARY

The blood vessel dissection apparatus, systems and methods described herein include features that may reduce direct vessel compression and longitudinal vessel stretching during the dissection process. In some embodiments, the elongated "bottle nose" shape of the dissection tips described herein may provide more atraumatic dissection of fine side branches (which are points where excessive branch stretching can result in branch avulsions and tissue micro fractures from the primary vessel).

In addition, some embodiments of the blood vessel dissection apparatus systems and methods described herein include a depression formed by concave surfaces in the dissection tip and shaft that may further reduce vessel contact as the dissection apparatus is advanced. In addition, trauma to side branches the main vessel trunk may be reduced by reducing friction, vessel compression and vessel stretching.

Further, in some embodiments, the apparatus systems and methods described herein may provide the ability to control fluid flow (e.g., the flow of carbon dioxide gas, etc.) into the tunnel created by a dissection device and/or occupied by a blood vessel harvesting apparatus. Control over the fluid flow and/or pressure during an endoscopic procedure may reduce the likelihood of over-pressurization within the subcutaneous tunnel compartment. That over-pressurization may, in some instances, lead to the development of carbon dioxide embolization (where carbon dioxide gas is the fluid being delivered) when, e.g., pressure gradients within the tunnel compartment exceed the central venous pressures of the patient.

The blood vessel harvesting apparatus described herein may be used to harvest blood vessels dissected using the vessel dissection apparatus, systems, and methods described herein or blood vessels that are dissected using any other suitable blood vessel dissection devices or methods.

In some embodiments, the blood vessel harvesting apparatus described herein may include a stabilizing member that can be used to hold a blood vessel in a fixed position during cautery and/or severing of the vessel.

The blood vessel harvesting apparatus described herein may provide potential advantages because of the ability, in some embodiments, to rotate an inner harvester shaft relative to the position of a cutting device. That rotation may potentially enhance the process of branch capture and engagement by reducing the amount of overall device rotation needed to capture and engage vessel tissue. In some embodiments, such a design may potentially allow the harvester to be maintained on top of a vessel without excessive rotation. That reduced rotation may potentially reduce (or in some cases minimize) rotational disorientation which occurs when excessive rotation (e.g., rotation of greater than 180 degrees) of the harvester shaft is required to approach and cut target tissue that in extreme oppositional orientation to the visual optics of the endoscope. Most endoscopic vessel harvesters of commercially available systems deploy cutting instruments from a fixed orientation point on the harvester device. That fixed position often requires excessive rotation to approach a vessel branch for capture and/or cutting. The rotating inner and outer shafts described in connection with the blood vessel harvesting apparatus described herein may allow for a more direct and anatomically correct stabilization of vessel tissue by reducing the need to rotate the inner harvester shaft, while allowing complete rotational capability of the outer harvester body to provide precise cutting of any tissue in a circumferential 360 degree plane. As noted above, rotation of the outer harvester body may potentially enhance the process of branch capture and engagement by reducing the amount of device rotation needed to capture and engage vessel tissue. In some embodiments, such a design may potentially allow the harvester to be maintained on top of a vessel without rotation, requiring minute amounts of later sliding of the device anterior to the vessel surface to capture vessel tissue in an anterior and lateral orientation plane. Such a design could potentially function in a more simplistic, precise, and ergonomic manner, potentially reducing or minimizing the need for excessive device rotation.

In one aspect, some embodiments of the vessel dissection apparatus described herein may include: a shaft comprising a proximal end and a distal end, wherein a longitudinal axis extends through the shaft from the proximal end to the distal end; and a dissection tip attached to the distal end of the shaft, wherein the dissection tip comprises a distal zone, an intermediate zone, and a proximal zone aligned along the longitudinal axis, wherein the intermediate zone is located between the proximal zone and the distal zone. The distal zone comprises a proximal end at which the distal zone meets a distal end of the intermediate zone, and wherein the dissection tip optionally comprises a non-circular cross-sectional shape at the proximal end of the distal zone. The intermediate zone of the dissection tip comprises an elongated concavo-convex cross-sectional shape that increases in cross-sectional area when moving from the distal end of the intermediate zone to a proximal end of the intermediate zone. The proximal zone of the dissection tip comprises an elongated concavo-convex cross-sectional shape that decreases in cross-sectional area when moving from a distal end of the proximal zone to a proximal end of the proximal zone. The shaft comprises an elongated concavo-convex cross-sectional shape at its distal end, wherein the concavo-convex cross-sectional shape extends proximally towards the proximal end of the shaft. The elongated concavo-convex cross-sectional shapes of the intermediate zone of the dissection tip, the proximal zone of the dissection tip, and the shaft align along the longitudinal axis to form a continuous depression extending proximally from the intermediate zone of the dissection tip into the shaft.

In some embodiments of the vessel dissection apparatus, the shaft comprises a lumen extending through the shaft to an opening at the distal end of the shaft, and wherein a distal seal element closes the lumen proximate the distal end of the shaft, wherein the seal element comprises a passage such that a device can be advanced distally through the passage from the lumen and retracted proximally from the lumen. In some embodiments, a proximal seal element closes the lumen proximate the proximal end of the shaft, wherein the proximal seal element comprises a passage such that a device can be advanced distally through the passage into the lumen and retracted proximally out of the lumen. In some embodiments, the proximal end of the shaft is attached to a handle, and wherein the lumen in the shaft is in fluid communication with a cavity in the handle. In some embodiments, a proximal seal element closes the cavity in the handle, wherein the proximal seal element comprises a passage such that a device can be advanced distally through the passage into the cavity and the lumen of the shaft and retracted proximally out of the cavity.

In some embodiments of the vessel dissection apparatus described herein, the shaft comprises a plurality of openings formed through a wall of the shaft, wherein fluid introduced into the lumen can exit from the lumen through at least one opening of the plurality of openings. In some embodiments, a majority of the plurality of openings are located in the depression formed by the elongated concavo-convex cross-sectional shape of the shaft. In some embodiments, at least one opening of the plurality of openings is located closer to the proximal end of the shaft than the distal end of the shaft.

In some embodiments of the vessel dissection apparatus described herein, the shaft comprises an elongated slot-shaped opening formed through a wall of the shaft, wherein the elongated slot-shaped opening is located in the depression formed by the elongated concavo-convex cross-sectional shape of the shaft, and wherein fluid introduced into the lumen can exit from the lumen through the elongated slot-shaped opening.

In some embodiments of the vessel dissection apparatus described herein, a fluid port is in fluid communication with the lumen such that fluid can be introduced into the lumen through the fluid port.

In some embodiments of the vessel dissection apparatus described herein, a pressure monitoring port is provided, wherein the pressure monitoring port is located along an exterior of the shaft between the proximal end and the distal end of the shaft, and wherein the pressure monitoring port comprises a monitoring lumen extending proximally towards the proximal end of the shaft. In some embodiments, a pressure monitoring device is attached to a proximal end of the monitoring lumen to monitor fluid pressure at the pressure monitoring port.

In one aspect, some embodiments of the blood vessel harvesting apparatus described herein may include an inner shaft comprising a proximal end and a distal end, the inner shaft extending between the proximal end and the distal end; an outer shaft comprising a first lumen and a second lumen, wherein at least a portion of the inner shaft is located within the first lumen, and wherein the inner shaft and the outer shaft are configured to rotate relative to each other about a longitudinal axis extending between the proximal end and the distal end of the inner shaft while the inner shaft is located within the first lumen, and further wherein the first lumen and the second lumen each comprise an opening proximate a distal end of the outer shaft; an optional cutting instrument comprising a cutting device located at the distal end of a delivery body, wherein at least a portion of the cutting instrument is located within the second lumen of the outer shaft; a capture member proximate the distal end of the inner shaft, wherein the capture member is operably attached to struts extending through the inner shaft, and wherein the capture member and the struts are movable between a retracted position in which the capture member is located proximate the distal end of the inner shaft and an extended position in which a blood vessel aperture is defined between the distal end of the inner shaft and the capture member, and wherein the capture member comprises a vessel gate that is movable between an open position in which a blood vessel can enter the blood vessel aperture and a closed position in which a blood vessel located in the blood vessel aperture is captured between the capture member and the distal end of the inner shaft; and a stabilizing member located in the blood vessel aperture, wherein the stabilizing member is movable between a retracted position in which the stabilizing member is located proximate the distal end of the inner shaft and an extended position in which the stabilizing member is located proximate the capture member when the capture member is in its extended position, wherein the stabilizing member spans the blood vessel aperture between the distal end of the inner shaft and the capture member, and wherein the stabilizing member is slidably attached to the struts of the capture member such that the stabilizing member slides along the struts when moving between the retracted position and the extended position when the capture member is in its extended position.

In some embodiments of the blood vessel harvesting apparatus described herein, the inner shaft and the outer shaft rotate 360 degrees about the longitudinal axis relative to each other.

In some embodiments of the blood vessel harvesting apparatus described herein, the opening of the second lumen is in a fixed position relative to the opening of the first lumen.

In some embodiments of the blood vessel harvesting apparatus described herein, the vessel gate comprises a rotating member that rotates between the open position and the closed position.

In some embodiments of the blood vessel harvesting apparatus described herein, the vessel gate comprises a member that moves distally and/or proximally to move the vessel gate between the open position and the closed position.

In some embodiments of the blood vessel harvesting apparatus described herein, the capture member comprises two vessel gates, wherein each vessel gate is movable between an open position in which a blood vessel can enter the blood vessel aperture and a closed position in which a blood vessel located in the blood vessel aperture is captured between the capture member and the distal end of the inner shaft. In some embodiments, each vessel gate comprises a separate rotating member such that each vessel gate can be moved between the open and closed positions independently of the other vessel gate. In some embodiments, the capture member comprises a common rotating member, wherein rotation of the common rotating member moves both of the vessel gates between the open and closed positions.

In some embodiments of the blood vessel harvesting apparatus described herein, each vessel gate comprises a member that moves distally and/or proximally to move the vessel gate between the open position and the closed position.

In some embodiments of the blood vessel harvesting apparatus described herein, the cutting device of the cutting instrument is movable from a retracted position in which the cutting device is located within the second lumen of the outer shaft and an extended position in which the cutting device is located outside of the second lumen proximate the blood vessel aperture.

In some embodiments of the blood vessel harvesting apparatus described herein, the distal end of the inner shaft comprises a capture member slot, wherein the capture member is located at least partially within the capture member slot when the capture member is in its retracted position.

In some embodiments of the blood vessel harvesting apparatus described herein, the inner shaft comprises an endoscope lumen that comprises an opening at the distal end of the inner shaft.

In a second aspect, some embodiments of a method of assembling and testing a blood vessel harvesting apparatus as described herein may include: positioning at least a portion of the inner shaft within the outer shaft; advancing the capture member relative to the inner shaft until the capture member is in its extended position; moving the vessel gate between its open and closed positions; moving the stabilizing member between its retracted position and its extended position when the capture member is in its extended position; rotating the inner shaft and the outer shaft relative to each other about the longitudinal axis; and optionally advancing the cutting device of the cutting instrument out of the opening of the second lumen.

In a third aspect, some embodiments of the blood vessel harvesting apparatus described herein may include a harvester shaft comprising a lumen dimensioned for receiving an endoscope; a head portion attached to a distal end of the harvester shaft, wherein the head portion comprises a cap and a support member, wherein the cap and the support member define a capture slot between the distal end of the harvester shaft and the cap, wherein the capture slot comprises a proximal end proximate the distal end of the harvester shaft and a distal end proximate the cap; a control member extending through the harvester shaft, wherein the control member is extendable from a retracted position in which a distal end of the control member is located proximate the proximal end of the capture slot and an extended position in which the distal end of the control member is located proximate the cap, and wherein the control member extends across the capture slot to close the capture slot when the control member is in the extended position; and a stabilizing member located in the capture slot, wherein the stabilizing member is movable between a retracted position in which the stabilizing member is located proximate the distal end of the harvester shaft and an extended position in which the stabilizing member is located proximate the cap, wherein the stabilizing member spans the capture slot between the control member and the support member, and wherein the stabilizing member is slidably attached to both the control member and the support member such that the stabilizing member slides along the control member and the support member when moving between the retracted position and the extended position.

In some embodiments of the blood vessel harvesting apparatus according to the third aspect, the support member extends through the harvester shaft such that the capture slot is in the form of an annular slot that extends around the support member between the cap and the distal end of the harvester shaft; and the apparatus comprises a second control member extending through the harvester shaft, wherein the second control member is extendable from a retracted position in which a distal end of the second control member is located proximate the proximal end of the capture slot and an extended position in which the distal end of the second control member is located proximate the cap, and wherein the second control member extends across the capture slot to close the capture slot when the control member is in the extended position; and further wherein the stabilizing member also spans the capture slot between the second control member and the support member, and wherein the stabilizing member is slidably attached to both the second control member and the stabilizing member such that the stabilizing member slides along the second control member and the support member when moving between the retracted position and the extended position.

In some embodiments of the blood vessel harvesting apparatus according to the third aspect, a blood vessel cutting instrument is located within the harvester shaft, and wherein the blood vessel cutting instrument can be advanced into the capture slot from a retracted position within the harvester shaft.

In some embodiments of the blood vessel harvesting apparatus according to the third aspect, the stabilizing member is attached to a stabilizing member actuator that extends proximally through the harvester shaft from the stabilizing member.

In some embodiments of the blood vessel harvesting apparatus according to the third aspect, the stabilizing member comprises a control member aperture at one end, wherein the control member extends through the control member aperture.

In some embodiments of the blood vessel harvesting apparatus according to the third aspect, the support member comprises a guide rod, and wherein the stabilizing member comprises a guide rod aperture at one end, wherein the guide rod extends through the control member aperture.

In some embodiments of the blood vessel harvesting apparatus according to the third aspect, the apparatus comprises an outer shaft that comprises a first lumen and a second lumen, wherein at least a portion of the harvester shaft is located within the first lumen of an outer shaft the harvester shaft, wherein the harvester shaft and the outer shaft are configured to rotate relative to each other about a longitudinal axis extending through the first lumen while the harvester shaft is located within the first lumen, and further wherein the first lumen and the second lumen each comprise an opening proximate a distal end of the outer shaft. In some embodiments, the apparatus further comprises a cutting instrument comprising a cutting device located at the distal end of a delivery body, wherein at least a portion of the cutting instrument is located within the second lumen of the outer shaft.

In a fourth aspect, some embodiments of a method of assembling and testing a blood vessel harvesting apparatus as described herein may include: moving the control member between its retracted position and its extended position; and moving the stabilizing member in the capture slot between its retracted position and its extended position when the control member is in its extended position. In some embodiments, the method may further include positioning at least a portion of the harvester shaft in the first lumen of the outer shaft; rotating the harvester shaft and the outer shaft relative to each other about the longitudinal axis; and optionally advancing a cutting device of a cutting instrument out of the opening of the second lumen.

The above summary is not intended to describe each embodiment or every implementation of any apparatus, systems and methods described herein. Rather, a more complete understanding of any apparatus, systems and methods described herein will become apparent and appreciated by reference to the following Description of Illustrative Embodiments and claims in view of the accompanying figures of the drawing.

DESCRIPTION OF ILLUSTRATIVE EMBODIMENTS

In the following description of illustrative embodiments described herein, reference is made to the accompanying figures of the thawing which form a part hereof, and in which are shown, by way of illustration, specific embodiments which may be practiced. It is to be understood that other embodiments may be utilized and structural changes may be made without departing from the scope of the present invention.

The vessel dissection and harvesting apparatus, systems, and methods described herein may be used in combination with each other or they may be used separately. For example, a blood vessel may be dissected using the dissection apparatus, systems, and methods described herein, followed by harvesting of the dissected vessel using the harvesting apparatus, systems, and methods described herein. Alternatively, a blood vessel may be dissected using the dissection apparatus, systems, and methods described herein, but harvested using a different harvesting apparatus, system, and method. In another alternative, a blood vessel dissected using a dissection apparatus, system and method other than those described herein may be harvested using the harvesting apparatus, systems, and methods described herein.

Dissection Apparatus, Systems, and Methods

Figure 1:
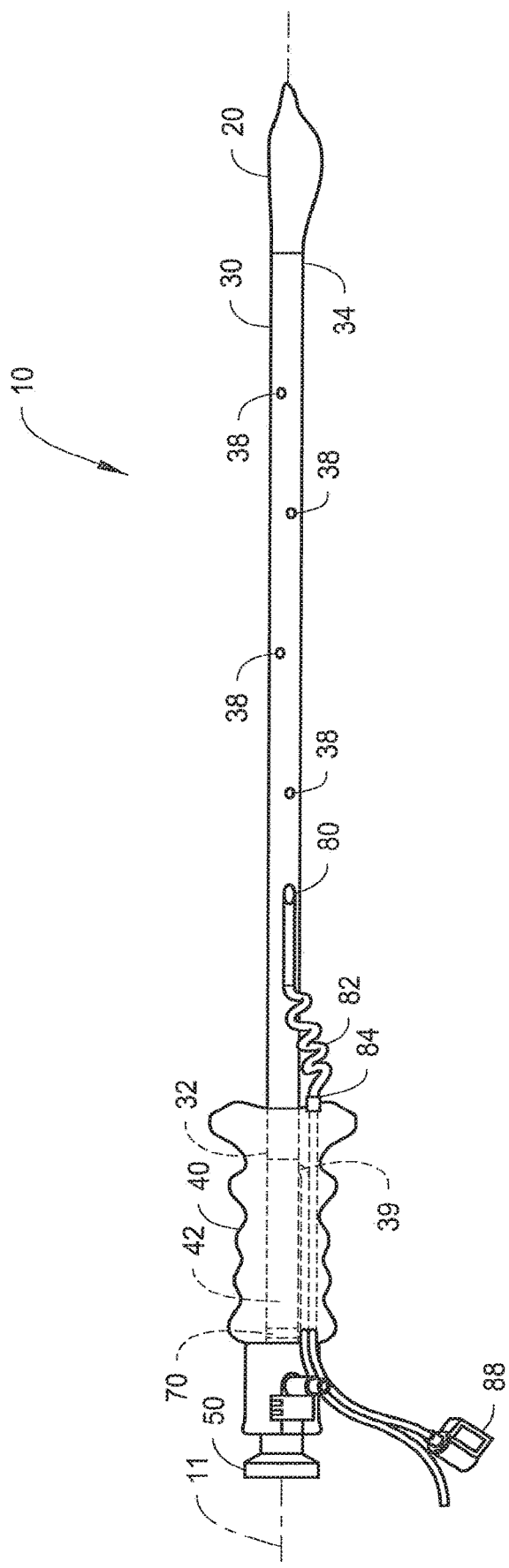
FIG. 1 depicts one illustrative embodiment of a vessel dissection apparatus as described herein.

Referring to FIG. 1, one embodiment of a vessel dissection apparatus 10 is depicted. The illustrative embodiment of vessel dissection apparatus 10 depicted in FIG. 1 includes a dissection tip 20, shaft 30 and handle 40. An endoscope 50 is depicted in position in the handle 40, with the endoscope 50 being inserted into the shaft 30 as described herein.

The shaft 30 has a proximal end 32 and a distal end 34, wherein a longitudinal axis 11 extends through the shaft 30 from the proximal end to the distal end. The dissection tip 20 is located at the distal end 34 of the shaft 30.

Figure 2:
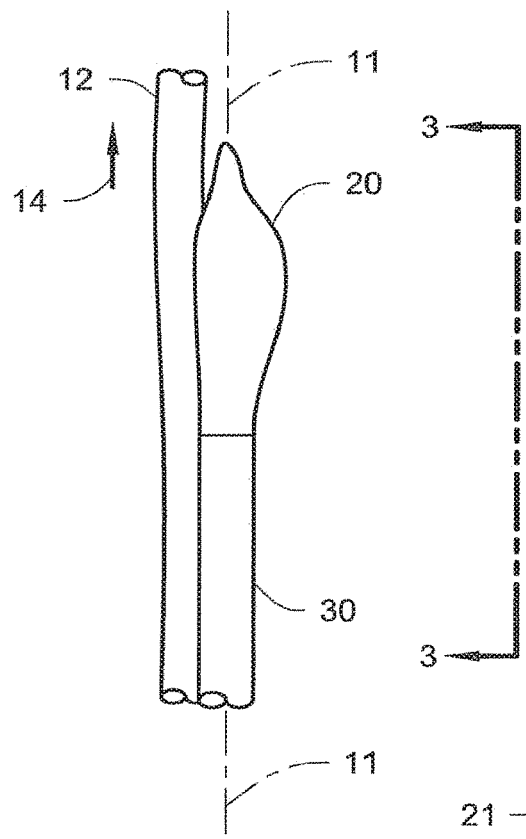
FIG. 2 is an enlarged view of the dissection tip and shaft advancing along a blood vessel.

The distal end of the vessel dissection apparatus 10 is depicted in FIG. 2 during advancement of the apparatus 10 over a blood vessel 12 (or other tubular structure which may need to be dissected from surrounding tissue). The advancement in the direction of arrow 14 may be described as advancement in the distal direction as discussed herein.

Figure 3:
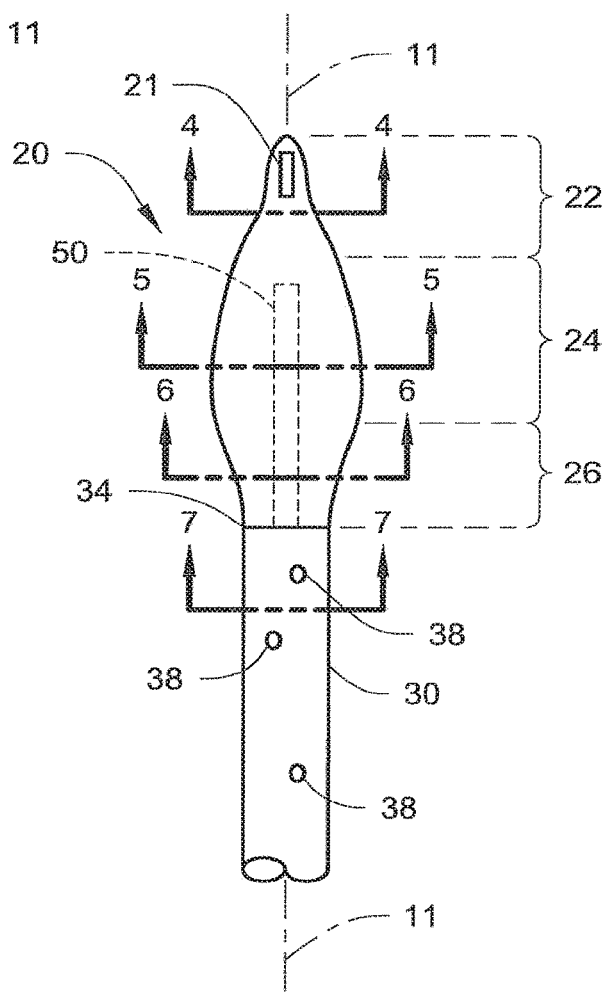
FIG. 3 is a view of the dissection tip and shaft of FIG. 2 taken along line 3-3 in FIG. 2 with the vessel removed for clarity and with an endoscope advanced out of the distal end of the shaft.

Referring to FIG. 3, which is a view of the dissection tip 20 and shaft 30 of FIG. 2 taken along line 3-3 in FIG. 2 (with the vessel removed for clarity and with endoscope 50 advanced out of the distal end 34 of the shaft 30). The dissection tip 20 includes a distal zone 22, an intermediate zone 24, and a proximal zone 26 aligned along the longitudinal axis 11. The intermediate zone 24 is located between the proximal zone 26 and the distal zone 22.

The distal zone 22 includes a proximal end at which the distal zone 22 meets a distal end of the intermediate zone 24. The dissection tip 20 preferably has a non-circular cross-sectional shape at the proximal end of the distal zone 22.

Figure 4:
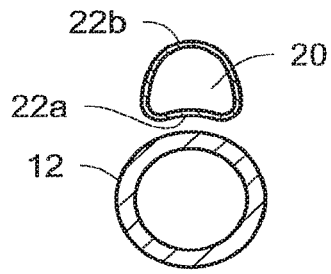
FIG. 4 is a cross-sectional view of the distal zone of the dissection tip of FIG. 3, taken along line 4-4 in FIG. 3.

FIGS. 4-7 are cross-sectional views taken in planes that are preferably transverse to the longitudinal axis 11. Referring to FIG. 4, one illustrative embodiment of a non-circular cross-sectional shape of the dissection tip 20 at the proximal end of the distal zone 22 is depicted with the vessel 12 included. It may be preferred that the non-circular cross-sectional shape of the distal end of the distal zone 22 be in the form of a concavo-convex cross-sectional shape where one surface 22a of the distal zone 22 of the dissection tip 20 is concave (next to the vessel 12) while the surface 22b on the opposite side of the distal zone 22 is convex.

Figure 5:
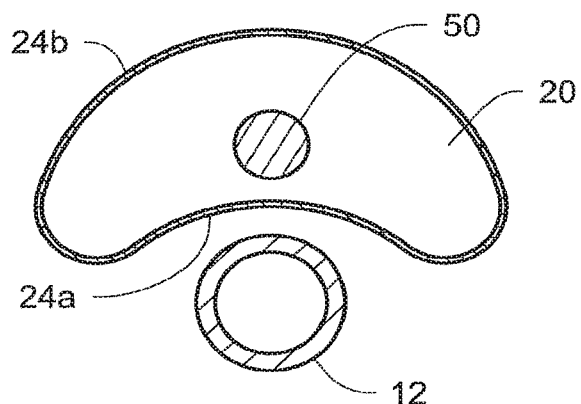
FIG. 5 is a cross-sectional view of the intermediate zone dissection tip of FIG. 3, taken along line 5-5 in FIG. 3.

The intermediate zone 24 of the dissection tip 20 includes a proximal end at which the intermediate zone 24 meets a distal end of the proximal zone 26. Referring to FIG. 5, the intermediate zone 24 of the dissection tip 20 has an elongated concavo-convex cross-sectional shape that increases in cross-sectional area when moving from the distal end of the intermediate zone 24 (i.e., where the intermediate zone 24 meets the distal zone 22) to a proximal end of the intermediate zone 24 (where the intermediate zone 24 meets the proximal zone 26). The elongated concavo-convex cross-sectional shape of the intermediate zone 24 includes a concave surface 24a (next to the vessel 12) and a convex surface 24b on the opposite side of the intermediate zone 24. The increase in cross-sectional area within the intermediate zone 24 may be continuous as depicted or it may be over only a part of the length of the intermediate zone 24 (where the length extends along the longitudinal axis 11). The endoscope 50 is also present in FIG. 5.

Figure 6:
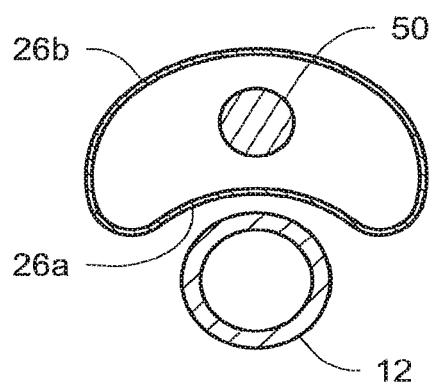
FIG. 6 is a cross-sectional view of the proximal zone of the dissection tip of FIG. 3, taken along line 6-6 in FIG. 3.

The proximal zone 26 of the dissection tip 20 includes a proximal end at which the proximal zone 26 meets the distal end 34 of the shaft 30. Referring to FIG. 6, the proximal zone 26 of the dissection tip 20 has an elongated concavo-convex cross-sectional shape that decreases in cross-sectional area when moving from the distal end of the proximal zone 26 (i.e., where the proximal zone 26 meets the intermediate zone 24) to a proximal end of the proximal zone 26 (i.e., where the proximal zone 26 meets the shaft 30). The elongated concavo-convex cross-sectional shape of the proximal zone 26 includes a concave surface 26a (next to the vessel 12) and a convex surface 26b on the opposite side of the proximal zone 26. The decrease in cross-sectional area within the proximal zone 26 may be continuous as depicted or it may be over only a part of the length of the proximal zone 26 (where the length extends along the longitudinal axis 11). The endoscope 50 is also present in FIG. 6.

Figure 7:
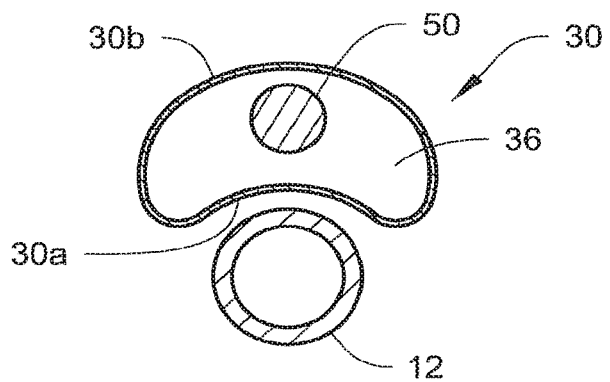
FIG. 7 is a cross-sectional view of the shaft of FIG. 3, taken along line 7-7 in FIG. 3.

The shaft 30 of the apparatus 10 described herein may also preferably include an elongated concavo-convex cross-sectional shape at its distal end 34 as depicted in FIG. 7. The elongated concavo-convex cross-sectional shape of the shaft 30 includes a concave surface 30a and a convex surface 30b on the opposite side of the shaft 30. The elongated concavo-convex cross-sectional shape of the shaft 30 extends proximally towards the proximal end 32 of the shaft 30. In various embodiments, the shaft 30 may have an elongated concavo-convex cross-sectional shape over all or only a part of its length between the proximal end 32 and the distal end 34 of the shaft 30. The endoscope 50 is also present in FIG. 7.

The elongated concavo-convex cross-sectional shapes of the distal zone 22 of the dissection tip 20 (if provided), the intermediate zone 24 of the dissection tip 20, the proximal zone 26 of the dissection tip 20, and the shaft 30 may preferably align along the longitudinal axis 11 to form a continuous depression extending proximally from the distal zone 22 and/or intermediate zone 24 of the dissection tip 20 into the shaft 30. That continuous depression may preferably ride over or straddle a vessel 12 (see, e.g., FIG. 2) during the dissection process.

In some embodiments, the dissection tips described herein may preferably be constructed of materials that are transparent and/or translucent such that objects (e.g., blood vessels) can be seen through the dissection tips to assist in navigating the dissection apparatus along a selected blood vessel during the dissection process. Examples of potentially suitable materials for the dissection tips may include, e.g., polycarbonates, etc.

In some embodiments, the distal zone 22 of the dissection tip 20 may include a visual indicator 21 (e.g., markings, a line, a shaded area, an insert molded into the dissection tip, etc.) visible from the ventral side of the dissection tip, i.e., the side of the distal zone 22 that is aligned with the convex surfaces 24b and 26b of the intermediate and proximal zones 24 and 26. The visual indicator 21 may preferably be aligned with the depression formed by the concave surfaces of the various components of the dissection tip 20. The visual indicator 21 can potentially be used to maintain proper alignment of the concave surfaces of the dissection tip 20 with the blood vessel being dissected such that the depression formed in the dissection tip 20 and shaft 30 are also aligned with the blood vessel during the dissection process.

The dissection tip 20 could, in some embodiments, include a coating of (or be constructed of) low surface energy material(s) that reduce friction. Examples of some potentially useful materials may include, e.g., polytretrafluoroethylene (PTFE), etc. It may be preferred that any such materials be transparent or at least translucent enough to allow for some visualization through the material.

In the illustrative embodiment depicted in FIGS. 1-8, the shaft 30 includes a lumen 36 extending through the shaft 30 to an opening at the distal end 34 of the shaft 30. A distal seal element 60 closes the lumen 36 proximate the distal end 34 of the shaft 30. The seal element 60 preferably includes a passage such that a device (e.g., an endoscope 50) can be advanced distally through the passage from the lumen 36 (see, e.g., FIG. 8) and retracted proximally into the lumen 36. The passage may be in the form of one or more slits, cuts, openings, etc.

In some embodiments, the distal seal element 60 in the shaft 30 may be in the form of, e.g., an internal plug 63 that may be encased on the proximal 62 and distal 64 ends with an elastomeric covering (e.g., rubber, silicone, etc.) in the form of a membrane, washer, etc. The proximal and distal ends 62 and 64 may be spaced apart from each other (by, e.g., a distance of 10-15 mm) with the internal plug 63 located therebetween.

The elastomeric coverings at the proximal and distal ends 62 and 64 of the seal may, in some embodiments, include an opening that is sized to maintain a tight seal around an endoscope or other device passing therethrough (e.g., a circular opening of, e.g., a 2-3 mm diameter). The outer shapes of the components of the seal element 60 may preferably be contoured to match the concavo-convex shape of the shaft 30.

The internal plug 63 may, in some embodiments, be made from, e.g., an absorbent material (e.g., a cotton fiber based product, etc.). A slit may be provided within the internal plug 63 to facilitate passage of, e.g., an endoscope through the internal plug 63. In some embodiments, the distal end of a device (e.g., an endoscope) that passes through the distal seal element 60 may be cleaned and/or dried as the distal end of the endoscope passes through the seal and exits into the cavity formed by the dissection tip 20. The material used in the seal element 60 may assist in those instances when a device, e.g., and endoscope, is extracted from the dissection apparatus and then reintroduced into the shaft through moisture that has accumulated during the period of initial dissection (in some instances, moisture can accumulate within the shaft and collect on the tip of an endoscope, causing fogging).

The vessel dissection apparatus described herein may also, in some embodiments, include a handle 40 at the proximal end 32 of the shaft 30. The handle 40 may preferably be ergonomically shaped. In some embodiments, the handle 40 may include a cavity 42 that is in fluid communication with the lumen 36 in the shaft 30.

Regardless of whether or not a handle is present, it may be preferred in some embodiments to include a proximal seal element 70 that closes the lumen 36 of the shaft 30 proximate the proximal end 32 of the shaft 30. In those embodiments that include a handle 40 having a cavity 42, the proximal seal element 70 may be located in the cavity 42 of the handle 40. The seal element 70 may be constructed of, e.g., an elastomeric (e.g., rubber, silicone, etc.) body in the faun of a membrane, washer, etc. The elastomeric body of the proximal seal 70 may, in some embodiments, include an opening that is sized to maintain a tight seal around an endoscope or other device passing therethrough (e.g., a circular opening of, e.g., a 2-3 mm diameter). It should, however, be understood that in some embodiments, the proximal seal element 70 may not be provided. In such embodiments, the fluid (e.g., carbon dioxide gas, etc.) delivered into the lumen 36 of the shaft 30 may exit through the proximal end of the device—either the handle 40 (if provided) or the proximal end 32 of the shaft 30 (if no handle is provided).

Figure 8:
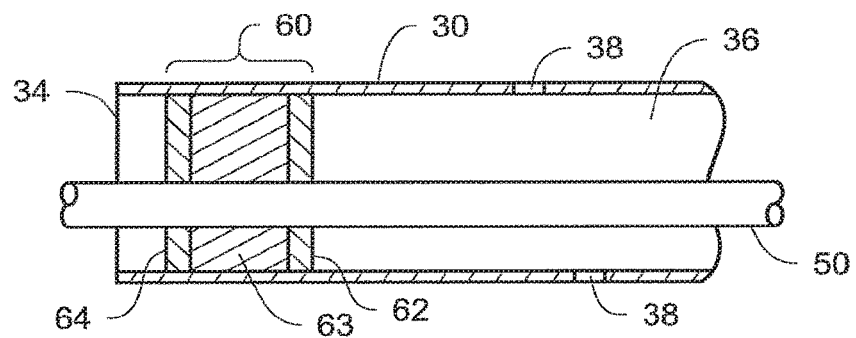
FIG. 8 is a cross-sectional view of one illustrative embodiment of a seal element located proximate the distal end of the shaft.

As discussed herein, the shaft 30 may include a lumen 36. Referring to FIGS. 1, 3, and 8, the shafts of the vessel dissection apparatus described herein may also preferably include a plurality of openings 38 formed through a wall of the shaft 30, such that fluid introduced into the lumen 36 of the shaft 30 can exit from the lumen 36 through at least one opening 38 of the plurality of openings 38. The fluid delivered using the lumen 36 and the openings 38 may include, e.g., carbon dioxide and/or other gases/liquids that may be used to create and/or enhance a working space around the vessel dissection apparatus.

The fluid supplied to the lumen 36 of the shaft 30 may be introduced into the apparatus through, e.g., a fluid port that is in fluid communication with the lumen 36. One illustrative embodiment of a fluid port may be seen in, e.g., FIGS. 1 and 10 where fluid port 39 is seen as opening into the cavity 42 in the handle 40. In embodiments of the dissection apparatus described herein that do not include a handle 40, the fluid port may open into the lumen 36 in the shaft 30.

It may be preferred, in some embodiments, that the openings 38 formed through the wall of the shaft 30 be located proximally from the dissection tip 20. In some embodiments, the openings may preferably be distributed over the entire length of the shaft such that fluid delivered through lumen 36 can exit the shaft 30 along substantially the entire length of the shaft 30. In some embodiments, at least one opening 38 may be located closer to the proximal end 32 of the shaft 30 than the distal end 34 of the shaft 30.

In some embodiments, a majority (or, in some cases, all) of the openings 38 may be located in the depression formed in the shaft 30 by the concave surface 32*a* of the elongated concavo-convex cross-sectional shape of the shaft 30.

Although the openings 38 are generally circular in shape, any openings provided in the shaft 30 to allow fluid to exit the lumen 36 may take any shape, e.g., oval, elliptical, rectangular, etc. For example, in some embodiments, the shaft 30 may include one or more elongated slot-shaped openings formed through the wall of the shaft 30 as seen in, e.g., FIG. 9. The one or more elongated slot-shaped openings may be located in the depression formed in the shaft 30.

Positioning one or more openings in the depression formed in the shaft 30 may potentially create a flow barrier of fluid (e.g., carbon dioxide gas, etc.) over a blood vessel, possibly allowing the apparatus to "float" over an infused layer of fluid. This could potentially provide clinical benefits such as, e.g., reducing contact of the dissection apparatus on the vessel surface.

Figure 10:
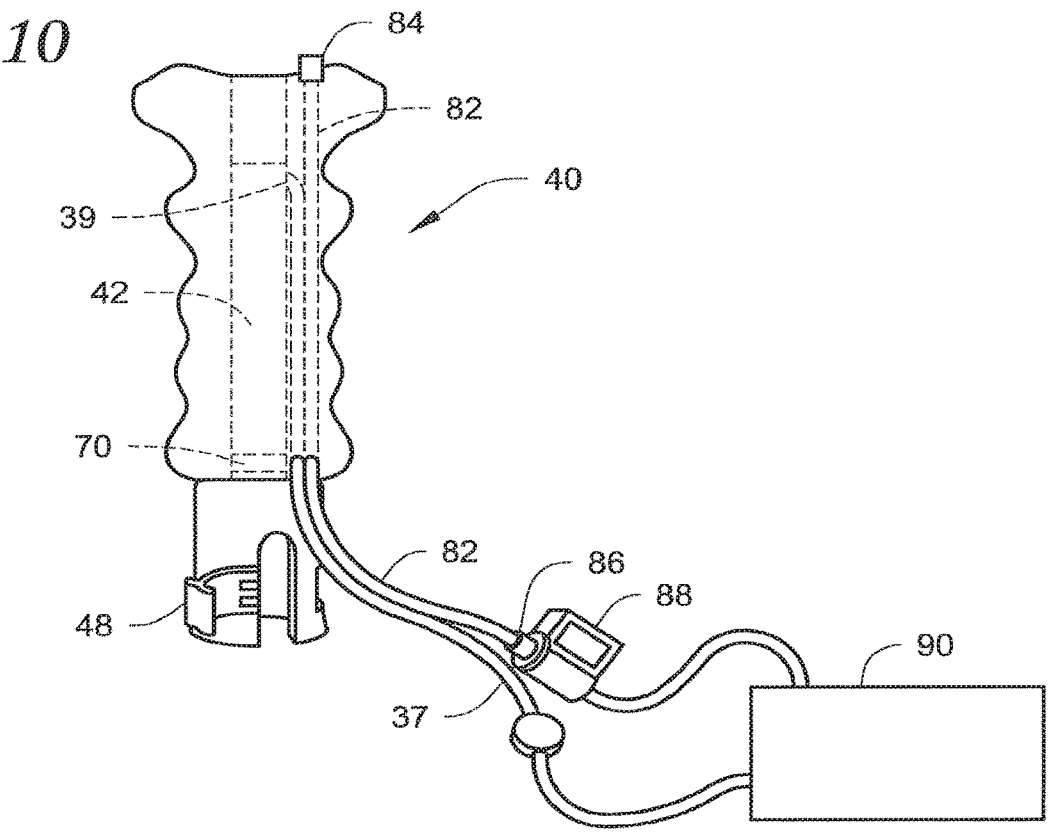
FIG. 10 is an enlarged view of one illustrative embodiment of a handle that may be attached to a shaft in a vessel dissection apparatus as described herein.

Referring to FIGS. 1, 10, and/or 12D, in some embodiments of the vessel dissection apparatus described herein, a pressure monitoring port 80 may be provided to monitor pressure within the cavity formed by the dissection apparatus 10. In the depicted illustrative embodiment, the pressure monitoring port 80 is located along an exterior of the shaft 30 between the proximal end 32 and the distal end 34 of the shaft 30. The pressure monitoring port 80 is preferably fluidly connected to a monitoring lumen 82 that extends proximally towards the proximal end 32 of the shaft 34.

Also in the depicted embodiment, the pressure monitoring lumen 82 extends through the handle 40. For those embodiments in which the shaft 30 and the handle 40 are provided as separate components that are connected together to the form the dissection apparatus 10, a fitting 84 may be provided along the monitoring lumen 82. The fitting 84 may, e.g., be located where the distal portion of the monitoring lumen 82 (i.e., the portion of the lumen 82 extending from port 80 to the fitting 84) connects to the proximal portion of the monitoring lumen 82 (i.e., the portion of the lumen 82 extending from fitting 84 towards the proximal end of the monitoring lumen 82).

The monitoring lumen 82 may continue proximally where it can be connected to, in some systems, a pressure monitoring device 88 is attached to the proximal end 86 of the monitoring lumen 82. The pressure monitoring device 88 may be used to monitor fluid pressure detected at the pressure monitoring port 80.

In some embodiments, the pressure monitoring device 88 may provide continuous measurements of internal subcutaneous tunnel pressures at the port 80. The pressure as measured by the pressure monitoring device 88 may, in some embodiments, provide valuable information regarding tunnel pressure which can be correlated to the patient's physiologic central venous pressure (monitored separately or integrated into the pressure monitoring device). The physiologic central venous pressure may be obtained by any known technique (e.g., a central venous catheter, Swan Ganz catheter, etc.).

Figure 11:
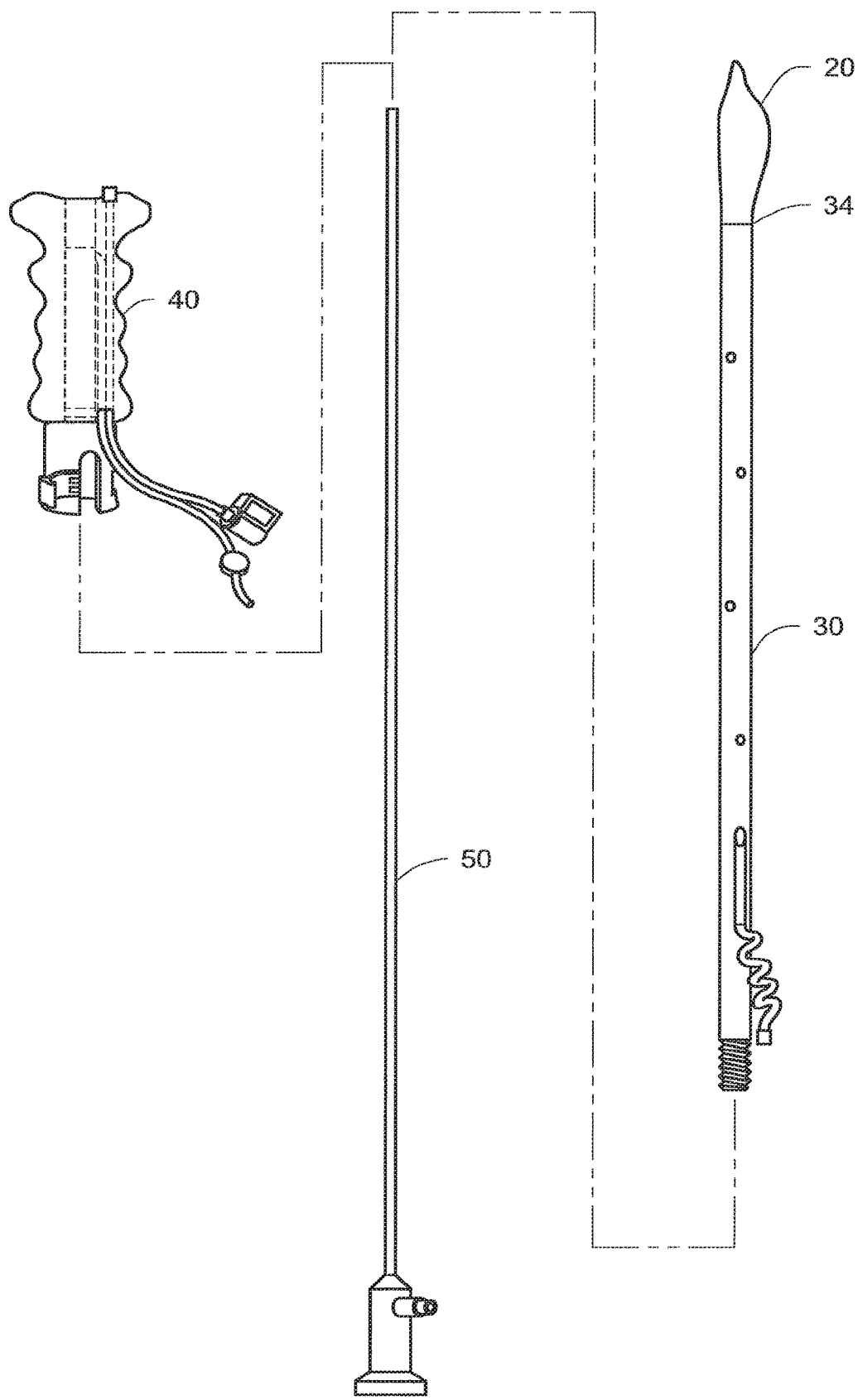
FIG. 11 depicts one illustrate vessel dissection system including a handle, endoscope, and shaft with dissection tip.

Referring to FIG. 11, the pressure monitoring device 88 connected to monitoring lumen 82 and pressure monitoring port 80 is depicted along with a fluid supply 90 that is connected by supply line 37 to the fluid port 39 that leads to lumen 36 and openings 38 in the shaft 30 as described herein. The pressure monitoring device 88 may, in some embodiments, be operatively connected to the fluid supply 90 such that the delivery of fluid from the fluid supply to the shaft 30 may be controlled based, at least in part, on the pressure measured by the pressure monitoring device 88 through pressure monitoring port 80. Control over the fluid delivery can be used, in some embodiments, to control fluid pressure within a tunnel formed by the dissection apparatus 10.

Control over the fluid delivery and, therefore, the fluid pressure within a tunnel formed by the dissection apparatus can be, in various embodiments, accomplished manually and/or automatically. In those embodiments in which the control is accomplished automatically, a separate controller may be operatively connected to both the pressure monitoring device 88 and the fluid supply 90 such that data or signals can be received and transmitted to accomplish the desired control of fluid delivery and/or pressure based, at least in part, on the pressure measured at the port 80. In a manually controlled system, some embodiments of the systems described herein may include adjustments in carbon dioxide flow using a flow gauge, dial, or valve mechanism, where the user can adjust or dial flow to maintain a finite variable control of pressure within the tunnel compartment below the physiologic central venous pressure of the patient.

Potential advantages of the ability to control fluid pressure within a tunnel formed as part of vessel dissection and/or harvesting process may, in some embodiments, reduce the diffusion of the fluid (e.g., carbon dioxide gas) delivered into the tunnel under pressure into the systemic circulation of a patient through, e.g., dissected and/or divided vascular tissue or structures. Additionally, the ability to control pressure and flow by the operator of dissection or other apparatus, independent of other care providers, may potentially reduce the events of carbon dioxide embolism during surgery, as unpredictable physiologic variables during major surgical procedures benefit those clinicians who can potentially adjust flow rates to compensate for changes in oxygen saturation and hemodynamics. This ability to, e.g., adjust carbon dioxide flow in response to changes in central venous pressure may improve patient safety and favor optimal clinical outcomes during minimally invasive procedures.

Although described in connection with vessel dissection and harvesting herein, it should be understood that control over the fluid flow and/or pressure delivered in response to changes in central venous pressure and/or other relevant physiologic parameters may be useful during any endoscopic procedure, e.g., general thoracic procedures, abdominal procedures, etc.

Referring to FIGS. 11 and 12A-12D, one illustrative embodiment of a method of assembling a blood vessel dissection apparatus as described herein is depicted. In the illustrated method, the dissection apparatus (see FIG. 11) includes a separate handle 40 and shaft 30 that are assembled together while the dissection tip 20 is depicted as pre-attached to the shaft. As discussed herein, however, in some embodiments no handle 40 may be provided, with the apparatus being manipulated at the proximal end using a shaft 30 alone. In other embodiments, the handle 40 and the shaft 30 may be pre-attached such that assembly of the handle 40 and the shaft 30 by a purchaser may not be required. As another alternative, although the dissection tip 20 is, in the depicted embodiment, pre-attached to the shaft 30, in other embodiments, the dissection tip 20 may need to be attached to the distal end 34 of the shaft 30.

Figure 12:
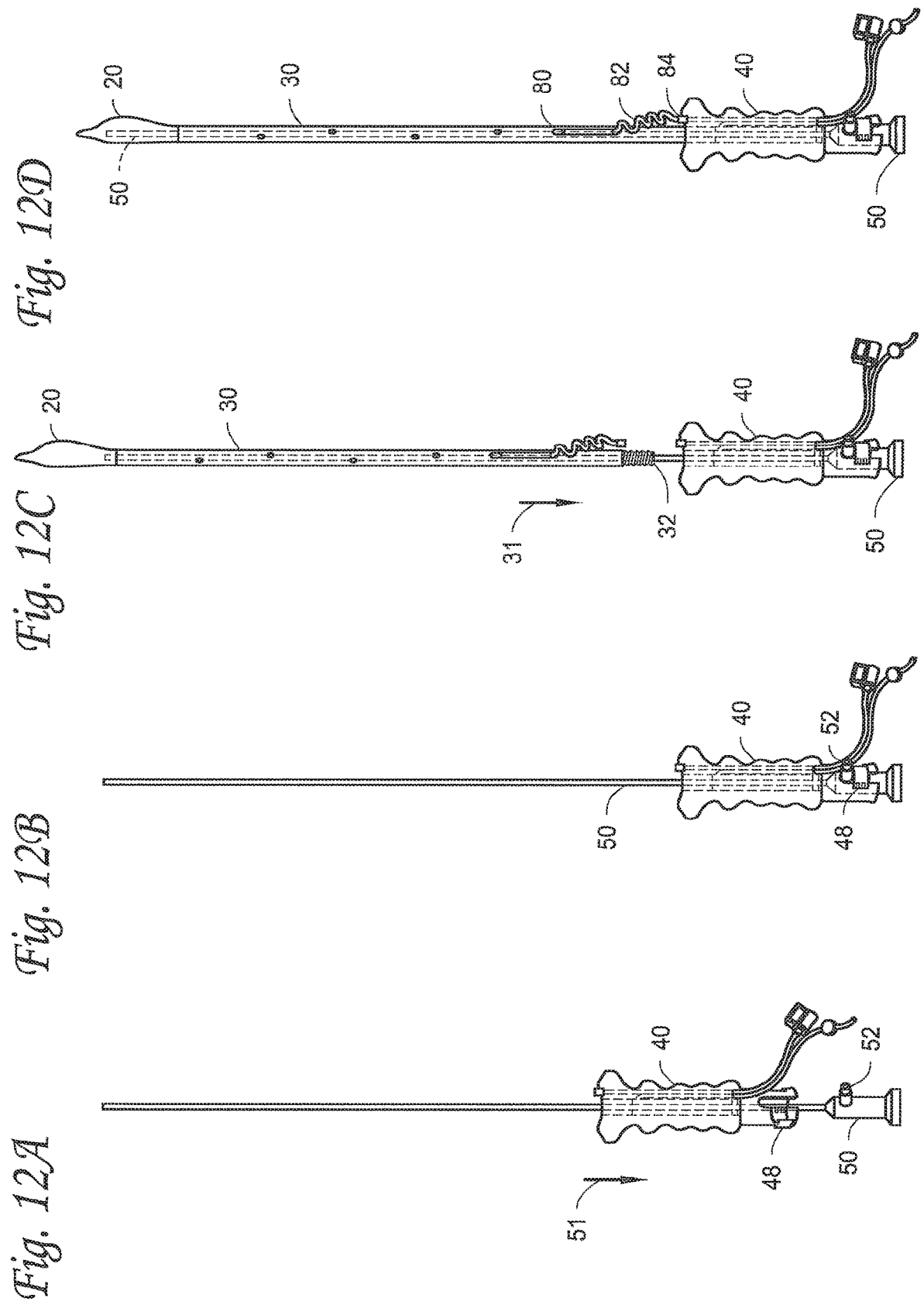
FIGS. 12A-12D depict one embodiment of assembling the vessel dissection system depicted in FIG. 11.

For the embodiment of the vessel dissection apparatus depicted in FIGS. 11 and 12A-12D, however, the assembly process may include mounting the handle 40 onto an endoscope by sliding the handle 40 over the endoscope 50 in the direction of arrow 51 in FIG. 12A. If the handle 40 includes a retention mechanism 48 in the form of, e.g., a slot and clamp or any other mechanism designed to hold the endoscope 50 and handle 40 in position relative to one another when assembled, the retention mechanism 48 may be open as seen in FIG. 12A. If the handle 40 includes a proximal seal element as described herein, the endoscope 50 may preferably pass tightly though the seal preventing fluid introduced into the shaft 30 from exiting through the handle 40. With the handle 40 in position at the proximal end of the endoscope 50, the retention mechanism 48 may be closed to hold the endoscope 50 and handle 40 in position relative to one another.

As seen in FIG. 12C, the shaft 30 and attached dissection tip 20 may then be positioned over the endoscope 50 such that the endoscope 50 passes through the distal seal element located at the distal end of the lumen in the shaft 30. The distal seal element preferably forms a seal around the endoscope 50 such that fluid in the lumen of the shaft 30 is forced to pass through the opening(s) in the shaft 30 as described herein rather than through the seal element past the endoscope 50.

The shaft 30 may, in some embodiments, be in the form of an elongated tube, with a proximal end 32 that includes a connector that allows the shaft 30 to form a fluid-tight seal with the handle 40 such that fluid introduced into the lumen of the shaft 30 does not escape through the shaft-handle junction. The connection between the shaft 30 and the handle 40 may be, e.g., a threaded connection or any other connection that snaps, locks, or otherwise engages the shaft and the handle together.

If provided in connection with the shaft 30, the proximal end of the monitoring lumen 82 may be connected to a connector 84 in the handle 40 such that the pressure monitoring device can be operably connected to the pressure monitoring port 80 as described herein.

Harvesting Apparatus, Systems and Methods

In the process of harvesting blood vessels, a vessel to be harvested may need to be dissected from the tissue surrounding the blood vessel, with the dissected vessel then being harvested using any compatible vessel harvesting apparatus. The vessel harvesting apparatus described herein may be used to harvest dissected blood vessels and/or blood vessels that do not require dissection before they are harvested.

Figure 13:
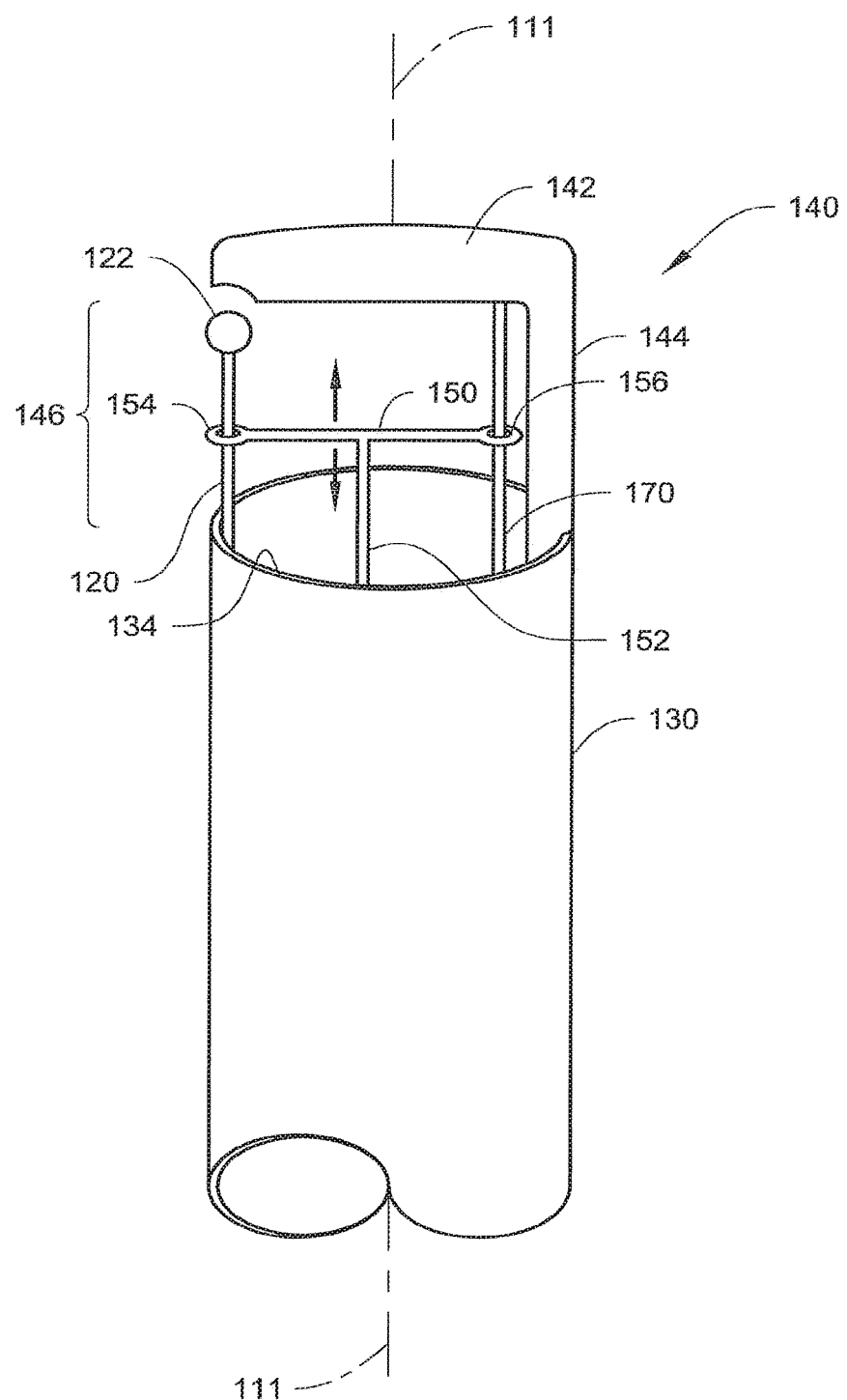
FIG. 13 depicts one illustrative embodiment of a blood vessel harvesting apparatus as described herein.
Figure 14:
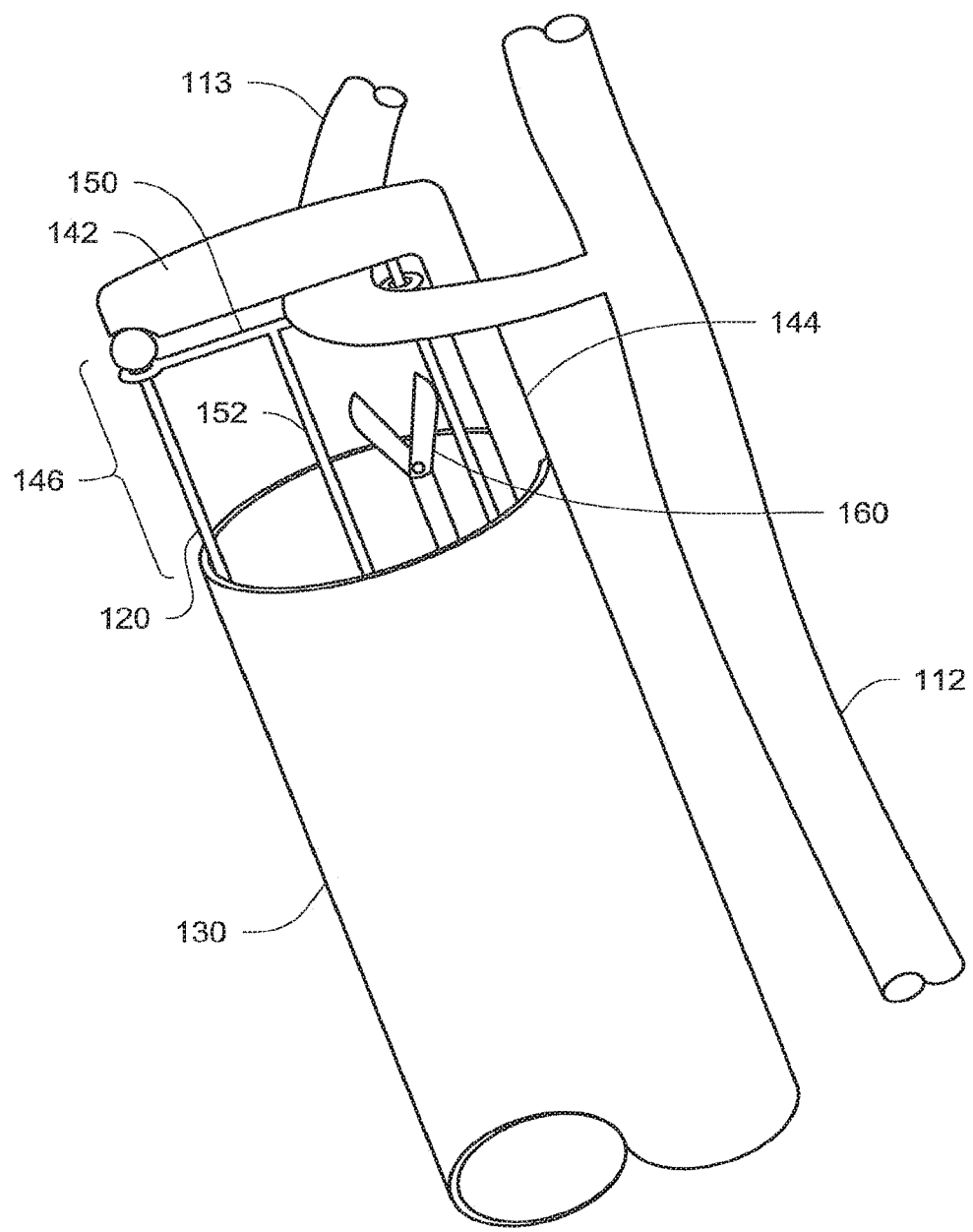
FIG. 14 is an alternate view of the harvesting apparatus of FIG. 13 in use.
Figure 15:
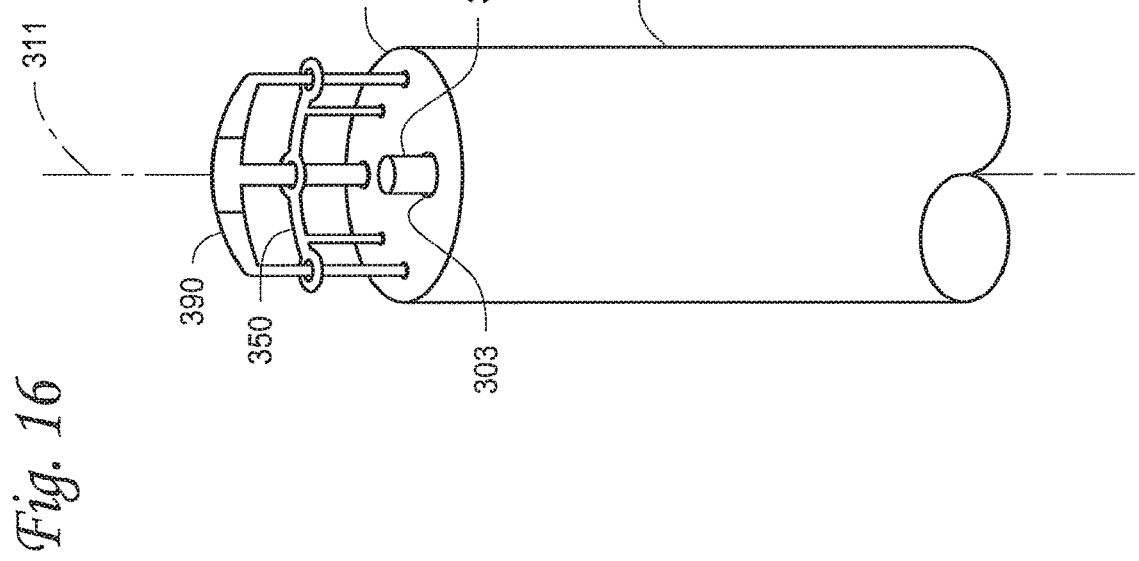
FIG. 15 depicts one alternate embodiment of a blood vessel harvesting apparatus as described herein.

One embodiment of a blood vessel harvesting apparatus as described herein is depicted in FIGS. 13-15. As seen in FIG. 13, the depicted embodiment of the blood vessel harvesting apparatus includes a harvester shaft 130 and a head portion 140 attached to a distal end 134 of the harvester shaft 140. The head portion 140 includes a cap 142 and a support member 144. The cap 142 and the support member 144 define a capture slot 146 between the distal end 134 of the harvester shaft 130 and the cap 142. The capture slot 146 has a proximal end proximate the distal end 134 of the harvester shaft 130 and a distal end proximate the cap 142.

The head portion 140 of the apparatus depicted in FIGS. 13 and 14 may be fixed in position relative to the harvester shaft 130 such that the length of the capture slot 146 is fixed (where the length of the capture slot 146 is measured along the longitudinal axis 111). Alternatively, the head portion 140 may be movable relative to the distal end 134 of the harvester shaft 130 such that the length of the capture slot 146 can be adjusted. An example of a harvesting apparatus with a movable head portion that could provide a capture slot with an adjustable length is described in, e.g., U.S. Pat. No. 7,556,633 (Lindsay).

In the embodiment of the harvesting apparatus depicted in FIGS. 13 and 14, a control member 120 extends through the harvester shaft 130. The control member 120 is extendable from a retracted position in which a distal end 122 of the control member 120 is located proximate the proximal end of the capture slot 146 to an extended position in which the distal end 122 of the control member 120 is located proximate the cap 142 and in which the control member 120 extends across the capture slot 146 to close the capture slot 146 when the control member 120 is in the extended position. The control member 120 may be in the form of, e.g., a rod or similar structural element.

The harvesting apparatus of FIGS. 13 and 15 also includes a stabilizing member 150 located in the capture slot 146. The stabilizing member 150 is movable between a retracted position in which the stabilizing member 150 is located proximate the distal end 134 of the harvester shaft 130 and an extended position in which the stabilizing member 150 is located proximate the cap 142. The stabilizing member 150 preferably spans the capture slot 146 (transverse to the longitudinal axis 111) between the control member 120 and the support member 144. In the depicted embodiment, the stabilizing member 150 is slidably attached to both the control member 120 and the support member 144 such that the stabilizing member 150 slides along the control member 120 and the support member 144 when moving between the retracted position and the extended position.

In some embodiments, movement of the stabilizing member 150 between the retracted and extended positions may be performed using attached to a stabilizing member actuator 152 that extends proximally through the harvester shaft 130 from the stabilizing member 150. The stabilizing member actuator 152 may be either advanced distally to move the stabilizing member 150 towards the cap 142 or withdrawn proximally to move the stabilizing member 150 towards the distal end 134 of the harvester shaft 130. It may be preferred that the actuator 152 be in the form of a rod that can be manipulated at the proximal end of the harvester shaft 130 by an operator.

In the harvesting apparatus described herein, the stabilizing member 150 may be used to act on a blood vessel branch 113 extending from a blood vessel 112 that is located within the capture slot 146 as depicted in, e.g., FIG. 14. The stabilizing member 150 may preferably hold the blood vessel branch 112 against the cap 142 to limit movement of the vessel 112 during the harvesting process. Vessel retraction, recoil, and laxity can, in some instances, result in excessive movement during the cauterizing process. Excessive movement may result in imprecise severing of branch vessels which can increase the risk of direct vessel injury and bleeding from improper engagement of the branch vessels when they are cut. In addition, excessive torque on the delicate blood vessels can potentially lead to branch avulsions from the primary vessel trunk which can adversely affect the integrity of the harvested blood vessel. Fixation of the branch vessels between, e.g., the stabilizing member 150 and the cap 142 can, in some instances, redirect vessel tension and stress forces away from the primary vessel trunk and more toward the tunnel wall, thus reducing the risk of direct vessel trauma during the harvesting process.

In some embodiments, a blood vessel cutting instrument 160 may be located within the harvester shaft 130. The blood vessel cutting instrument 160 can be advanced into the capture slot 146 from a retracted position within the harvester shaft 130. When advanced, the blood vessel cutting instrument 160 can be used to cut a blood vessel held in place by the stabilizing member 150 and the cap 142. In some embodiments, the cutting instrument 160 may also cauterize the cut vessels.

In some embodiments, such as the embodiment depicted in FIGS. 13 and 14, the stabilizing member 150 may include a control member aperture 154 at one end, wherein the control member 120 extends through the control member aperture 154 to guide movement of the stabilizing member 150 between the retracted and extended positions. The distal end 122 of the control member 120 may, in some embodiments, include a feature, e.g., a ball-shaped tip, etc. such that the stabilizing member 150 cannot slip off the end of the control member 120.

In some embodiments, the support member 144 may include a guide rod 170 and the stabilizing member 150 may include a guide rod aperture 156 at the end opposite from the control member 120. The guide rod 170 may preferably extend through the guide rod aperture 156 to assist in guiding movement of the stabilizing member 150 between the retracted and extended positions. Use of the guide rod 170 in addition to the control member 120 to support and guide the ends of the stabilizing member 150 may help to stabilize the stabilizing member and, thus, help the stabilizing member 150 to more securely hold a blood vessel extending through the capture slot 146.

Although a guide rod 170 is used in the depicted illustrative embodiment, it should be understood that any other suitable mechanism could be used to guide the end of the stabilizing member 150 closest to the support member 144. For example, the support member 144 itself could perform the function of the guide rod 170 with the stabilizing member being secured directly to the support member 144 (e.g., a slot could be provided in the support member 144, with the end of the stabilizing member 150 located in the slot, etc.).

One alternative embodiment of a harvesting apparatus as described herein is depicted in FIG. 15. In the depicted alternative embodiment, which includes a head portion 240 with a cap 242, the support member 244 may extend through the harvester shaft 230 such that the capture slot 246 is in the form of an annular slot that extends around the support member 244 between the cap 242 and the distal end 234 of the harvester shaft 230.

The alternative embodiment of FIG. 15 also includes a first and second control members 220a and 220b (referred to in common as control members 220), with both control members 220 extending through the harvester shaft 230. The control members are extendable from a retracted position in which the distal ends 222a and 222b of the control members 220 are located proximate the proximal end of the capture slot 246 (i.e., near the distal end 234 of harvester shaft 230) and an extended position in which the distal ends of the control members 220 are located proximate the cap 242. The control members 220 extend across the capture slot 246 to close the capture slot 246 in two locations when the control members are in their extended positions.

In the alternative embodiment of FIG. 15 the stabilizing member 250 also spans the capture slot 246 between the control members 220 and the support member 244. The ends of the stabilizing member 250 may preferably be slidably attached to both control members 220 as well as the support member 244 such that the stabilizing member 250 slides along and is guided by the control members 220 and the support member 244 when moving between the retracted position and the extended position. The stabilizing member 250 may be connected to a stabilizing member actuator 252 that can be used to move the stabilizing member 250 between the retracted and extended positions as described above.

Although not depicted in any one figure together, it should be understood that the harvester shafts of the embodiments described in connection with FIGS. 13-15 may be located within an outer shaft similar to that described in connection with the embodiments of the blood vessel harvesting apparatus depicted and described in connection with FIGS. 16-23D below. The potential advantages that may be achieved by such a combination as described herein may, in those instances, be achieved in connection with the apparatus of FIGS. 13-15 as well.

In addition to the various apparatus described herein in connection with FIGS. 13-15, methods of assembling and testing blood vessel harvesting apparatus as described herein may also be provided. The methods may include, for example, moving a control member 120 between its retracted position and its extended position; moving a stabilizing member 150 in the capture slot 146 between its retracted position and its extended position when the control member 120 is in its extended position. The methods may further include, in some embodiments, positioning at least a portion of a harvester shaft 130 in the first lumen of an outer shaft; rotating the harvester shaft 130 and the outer shaft relative to each other about the longitudinal axis; and, optionally, advancing a cutting device of the cutting instrument out of an opening of a second lumen in the outer shaft.

Figure 16:
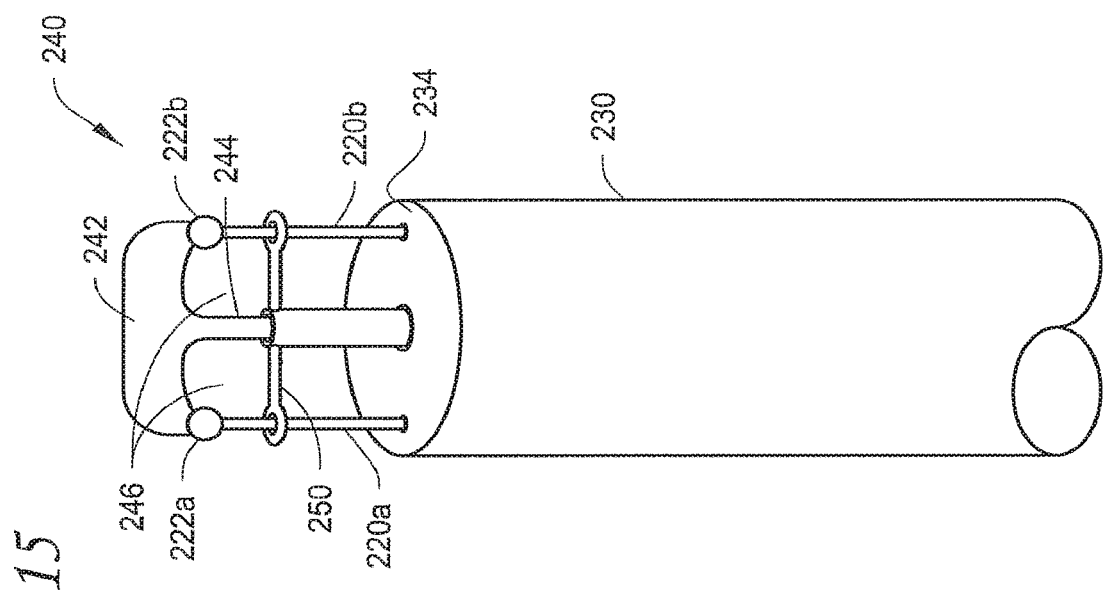
FIG. 16 is a perspective view of an illustrative embodiment of an inner harvester shaft of a blood vessel harvesting apparatus as described herein.
Figure 18:
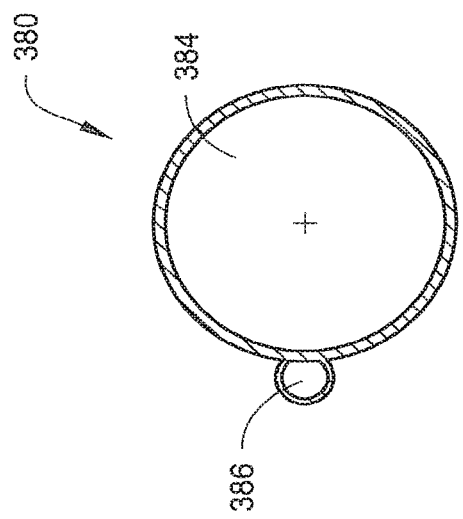
FIG. 18 is a cross-sectional view of the outer shaft of FIG. 17 taken along line 18-18 in FIG. 17.
Figure 17:
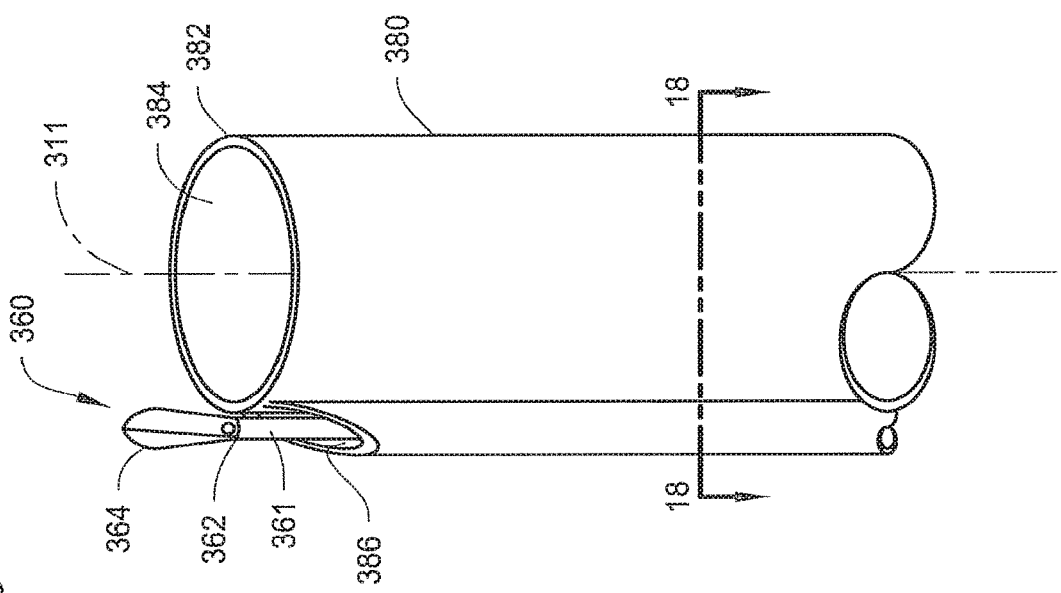
FIG. 17 is a perspective view of one embodiment of an outer shaft of a blood vessel harvesting apparatus as described herein.

Further embodiments of blood vessel harvesting apparatus are depicted in connection with FIGS. 16-11. In particular, FIGS. 16-21 depict various views of one illustrative embodiment of a blood vessel harvesting apparatus as described herein. The apparatus includes an inner shaft 330 (see, e.g., FIG. 16) and an outer shaft 380 (see, e.g., FIG. 18).

The inner shaft 330 includes a proximal end (not shown because only a distal portion of the inner shaft 330 is seen in FIG. 16) and a distal end 332. The inner shaft 330 may include a variety of other components that will be described in more detail below.

The outer shaft 380 includes a first lumen 384 and a second lumen 386. The first lumen 384 includes an opening 385 proximate the distal end 382 of the outer shaft 380 and the second lumen 386 includes an opening 387 proximate a distal end 382 of the outer shaft 380. When assembled into a blood vessel harvesting apparatus as described herein, at least a portion of the inner shaft 330 is located within the first lumen 384 of the outer shaft 380 (see, e.g., FIGS. 19 and 20).

The inner shaft 330 and the outer shaft 380 are configured to rotate relative to each other about a longitudinal axis 311 that extends through the inner shaft 330 (between its proximal and distal ends). That same axis also extends through the first lumen 384 of the outer shaft 380. The rotation between the inner shaft 330 and the outer shaft 380 occurs while at least a portion of the inner shaft 330 is located within the first lumen 384 of the outer shaft 380.

In some embodiments, the inner shaft 330 and the outer shaft 380 are capable of rotating three hundred sixty (360) degrees or more about the longitudinal axis 311 relative to each other. The rotation between the inner shaft 330 and the outer shaft 380 may be accomplished using any suitable structure and/or mechanism. One example of a potentially suitable structure may be found in, e.g., U.S. Pat. No. 6,749,572 (Edwardsen et al.).

In some embodiments, the opening of the second lumen 386 proximate the distal end 382 of the outer shaft 380 is in a fixed position relative to the opening of the first lumen 384. As used herein, "fixed position" means that the openings of the first lumen 384 and the second lumen 386 are always in the same positions relative to each other, i.e., their positions relative to each other cannot be changed without physically deforming the outer shaft 380.

The illustrative embodiment of the blood vessel harvesting apparatus depicted in FIGS. 16-21 also includes an optional cutting instrument 360 that includes a cutting device 364 located at the distal end 362 of a delivery body 361. It may be preferred that at least a portion of the cutting instrument 360 is located within the second lumen 386 of the outer shaft 380. The cutting instrument 360 may be in the form of a blood vessel cauterizing and cutting device that can be advanced out of the second lumen 386 from a retracted position within the second lumen 386. When advanced, the cutting instrument can be used to cut (and may optionally cauterize) a blood vessel held in place by the blood vessel harvesting apparatus as described herein. Examples of some potentially useful cutting devices and instruments may be found in, e.g., U.S. Pat. No. 6,749,609 (Lunsford et al.); U.S. Pat. No. 5,893,848 (Bales et al.); U.S. Pat. No. 5,891,140 (Ginn et al.); etc.

Another component of the illustrative embodiment of the blood vessel harvesting apparatus depicted in FIGS. 16-21 is a capture member 390 proximate the distal end 332 of the inner shaft 330, wherein the capture member 390 is operably attached to struts 391 extending through the inner shaft 330. The capture member 390 and its struts 391 are movable between a retracted position in which the capture member 390 is located proximate the distal end 332 of the inner shaft 330 and an extended position in which a blood vessel aperture 393 is defined between the distal end 332 of the inner shaft 330 and the capture member 390. It may be preferred that the capture member 390 be manipulated between its retracted and extended positions from the proximal end of the inner shaft 330 using any suitable mechanism that is operably connected to the capture member 390 (e.g., a hand-actuated slide dial, etc.).

Figure 20:
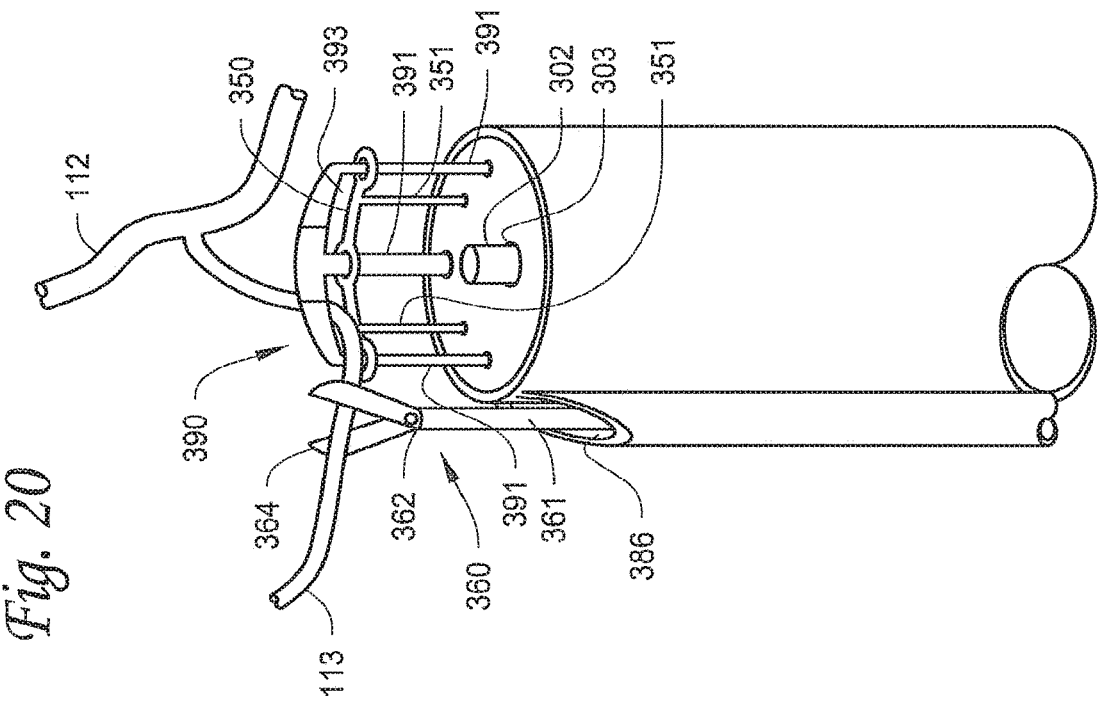
FIG. 20 is a perspective view of an illustrative embodiment of a blood vessel harvesting apparatus as described herein during capture and harvesting a blood vessel.

In the depicted embodiment, the capture member 390 includes a vessel gate 394 that is movable between an open position (as seen in, e.g., FIG. 21) in which a blood vessel can enter the blood vessel aperture 393 and a closed position (as seen in, e.g., FIGS. 16 and 20) in which a blood vessel branch 113 extending from a blood vessel 112 that is located in the blood vessel aperture 393 is captured between the capture member 390 and the distal end 332 of the inner shaft 330 (as seen in, e.g., FIG. 20).

In the depicted embodiment, the vessel gate 394 rotates about an axis that extends through the strut 391, although any other suitable action for opening and closing the vessel gate 394 may be provided in place of rotation of the vessel gate 394. Regardless of the mechanism used to provide a vessel gate 394 that is movable between an open and closed position, it may be preferred that the vessel gate be manipulated between its opened and closed positions from the proximal end of the inner shaft 330 using any suitable mechanism that is operably connected to the vessel gate (e.g., a hand-actuated slide dial, etc.).

Figure 19:
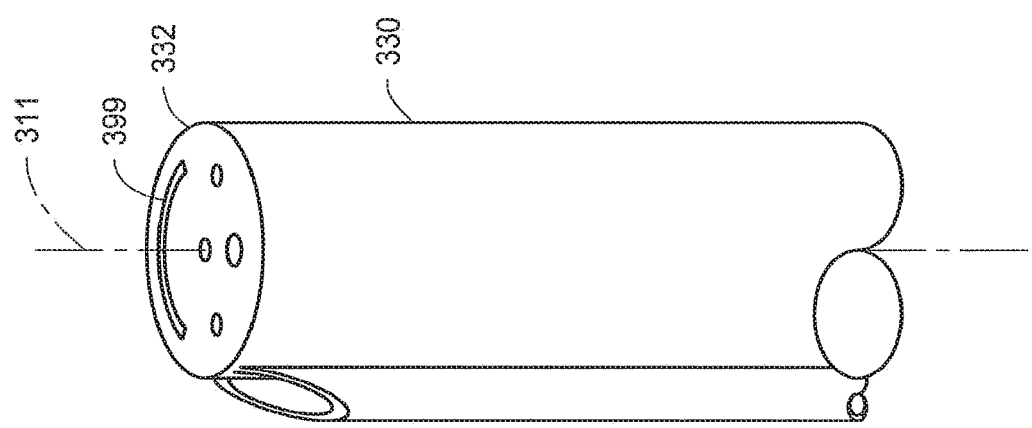
FIG. 19 is a perspective view of an illustrative embodiment of a blood vessel harvesting apparatus as described herein including a capture member slot.

Referring to FIG. 19, for example, in some embodiments, the distal end 332 of the inner shaft 330 comprises a capture member slot 399, wherein the capture member may be located at least partially within the capture member slot 399 when the capture member 390 is in its retracted position. The capture member slot 399 may provide some protection for the capture member 390 during advancement of the inner shaft to a selected internal location.

Figure 9:
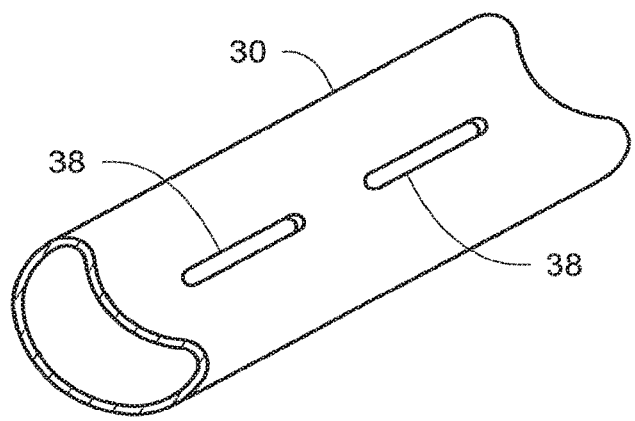
FIG. 9 depicts an illustrative embodiment of a portion of a shaft including openings in the form of elongated slots located in the depression formed in the concave side of the shaft.

Another component of the illustrative embodiment of the blood vessel harvesting apparatus depicted in FIGS. 16-9 is a stabilizing member 350 that is located in the blood vessel aperture 393 between the distal end 332 of the inner shaft 330 and the capture member 390. The stabilizing member 350 is movable between a retracted position in which the stabilizing member 350 is located proximate the distal end 332 of the inner shaft 330 (see, e.g., FIG. 21) and an extended position in which the stabilizing member 350 is located proximate the capture member 390 when the capture member 390 is in its extended position (see, e.g., FIG. 20). In some embodiments, the stabilizing member 350 spans the blood vessel aperture 393 (transverse to a longitudinal axis extending through the inner shaft 330) between the distal end 332 of the inner shaft 330 and the capture member 390. The stabilizing member 350 may preferably be slidably attached to the struts 391 of the capture member 390 such that the stabilizing member 350 slides along the struts 391 when moving between the retracted position and the extended position when the capture member 390 is in its extended position.

In some embodiments, movement of the stabilizing member 350 between the retracted and extended positions may be performed using the struts 351 that may preferably extend proximally through the inner shaft 330 from the stabilizing member 350. The stabilizing member 350 may be either advanced distally to move the stabilizing member 350 towards the capture member 390 or withdrawn proximally to move the stabilizing member 350 towards the distal end 332 of the inner shaft 330. It may be preferred that the stabilizing member 350 be manipulated between its retracted and extended positions from the proximal end of the inner shaft 330 using any suitable mechanism that is operably connected to the stabilizing member 350 (e.g., a hand-actuated slide dial, etc.).

In the blood vessel harvesting apparatus described herein, the stabilizing member 350 may be used to act on a blood vessel branch 113 extending from a blood vessel 112 that is located within the blood vessel aperture 393 as depicted in, e.g., FIG. 20. The stabilizing member 350 may preferably hold the blood vessel branch 112 against the capture member 390 to limit movement of the vessel 112 during the harvesting process. As seen in FIG. 20, a cutting instrument 360 may be advanced out of the second lumen 386 to cut (and optionally cauterize) a blood vessel 113 held in place by the stabilizing member 350 and the capture member 390. The cutting device 364 of the cutting instrument 390 is, in some embodiments, movable from a retracted position in which the cutting device 364 is located within the second lumen 386 of the outer shaft 380 and an extended position in which the cutting device 364 is located outside of the second lumen 386 proximate the blood vessel aperture 393.

Vessel retraction, recoil, and laxity can, in some instances, result in excessive movement during the cauterizing process. Excessive movement may result in imprecise severing of branch vessels which can increase the risk of direct vessel injury and bleeding from improper engagement of the branch vessels when they are cut. In addition, excessive torque on the delicate blood vessels can potentially lead to branch avulsions from the primary vessel trunk which can adversely affect the integrity of the harvested blood vessel. Fixation of the branch vessels between, e.g., the stabilizing member 350 and the capture member 390 can, in some instances, redirect vessel tension and stress forces away from the primary vessel trunk and more toward the tunnel wall, thus reducing the risk of direct vessel trauma during the harvesting process.

The blood vessel harvesting apparatus described herein may also include other components such as, e.g., a endoscope 302 that may be used to provide visual images to assist in positioning and operation of the blood vessel harvesting apparatus. The endoscope 302 may be located within an endoscope lumen 303. The location and positioning of any lumens used to deliver such additional devices may vary between devices, with the depicted embodiments constituting only one potential option among many.

Figure 21:
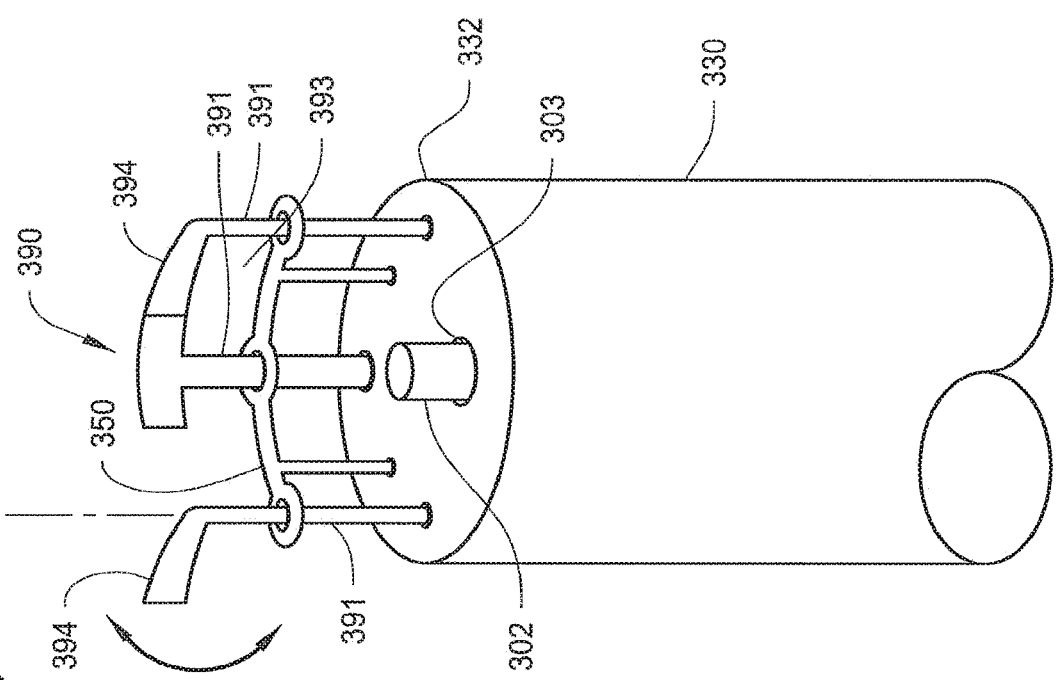
FIG. 21 is a perspective view of an illustrative embodiment of an inner harvester shaft of a blood vessel harvesting apparatus as described herein with a vessel gate in an open position.

In some embodiments such as that depicted in FIGS. 20 and 21, the capture member 390 may include two vessel gates 394, wherein each vessel gate 394 is movable between an open position in which a blood vessel can enter the blood vessel aperture 393 and a closed position in which a blood vessel located in the blood vessel aperture 393 is captured between the capture member 390 and the distal end 332 of the inner shaft 330.

Figure 22:
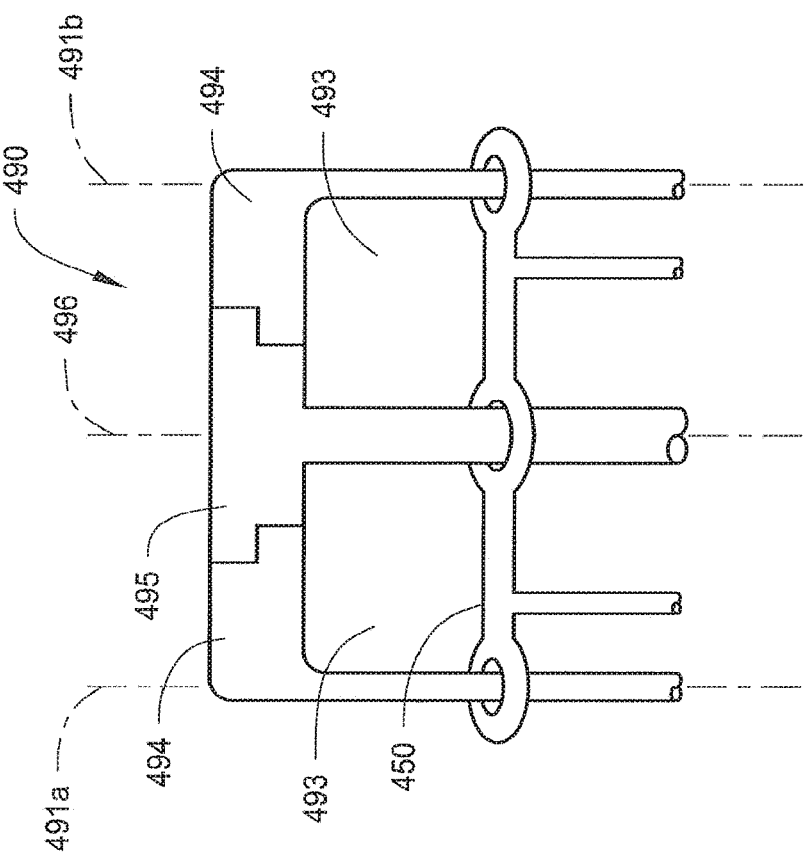
FIG. 22 is a perspective view of one illustrative embodiment of a capture member including two vessel gates and stabilizing member.

FIGS. 22 and 23A-23D depict some alternative embodiments of a capture member 490 that includes two vessel gates 494. Also seen in FIG. 22 is a stabilizing member 450. FIG. 22 is a perspective view, while FIGS. 23A-23D are top views taken along the axes of rotation of the various components seen in FIG. 22 (which, in the depicted embodiment are parallel—although such an arrangement is not required). The depicted vessel gates 494 each may preferably rotate around an axis 491a or 491b. Each vessel gate 494 includes a separate rotating member such that each vessel gate 494 can be moved between the open and closed positions independently of the other vessel gate 494 as depicted in, e.g., FIGS. 22B and 23C.

Figure 23A:
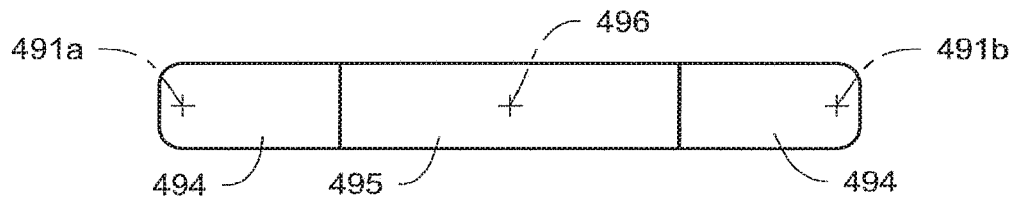
FIGS. 23A-23D are top views taken along the axes of rotation of the various components seen in FIG. 22.
Figure 23B:
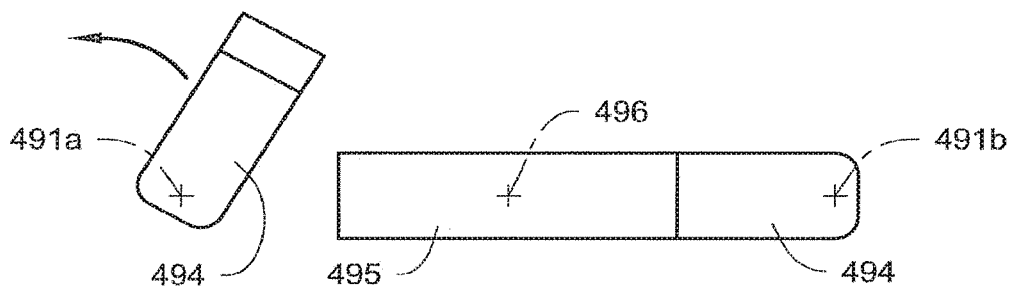
Figure 23C:
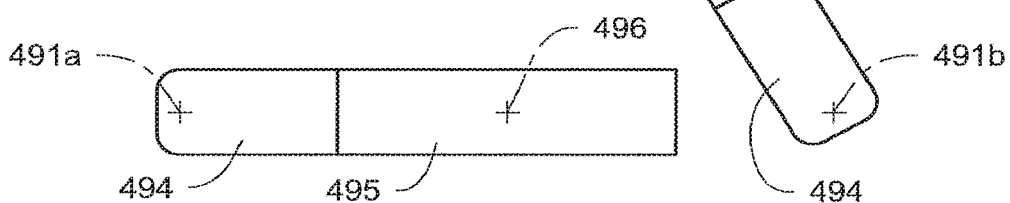
Figure 23D:
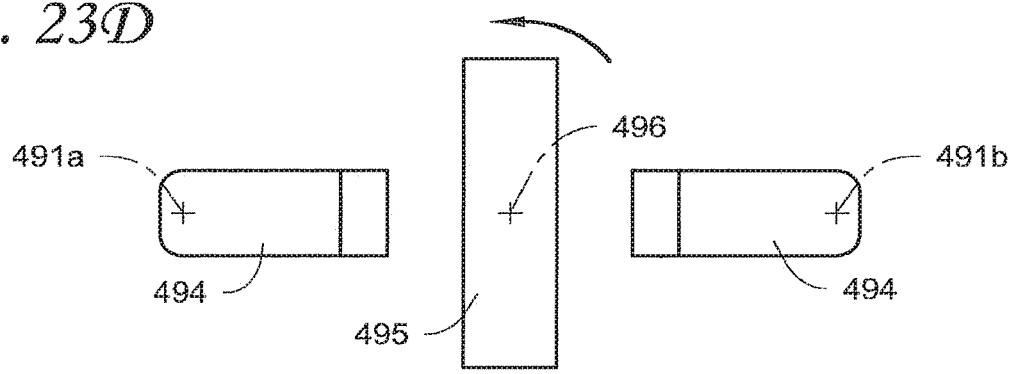

Alternatively, the capture member 490 may include a common rotating member 495, wherein rotation of the common rotating member 495 about an axis 496 moves both of the vessel gates 494 between the open and closed positions as seen in, e.g., FIG. 23D.

Figure 24:
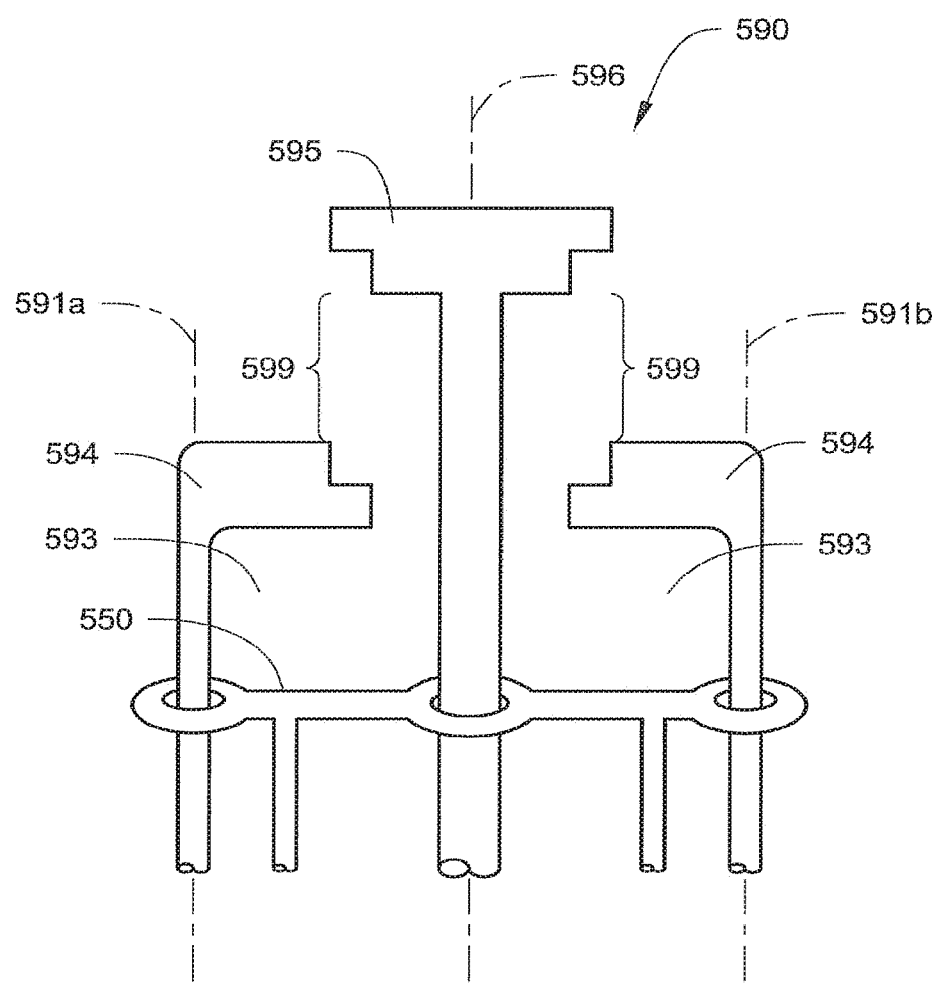
FIG. 24 is a perspective view of another illustrative embodiment of a capture member including two vessel gates and stabilizing member.

A structure similar to that depicted in FIG. 22 may, in at least one alternate embodiment, operate as depicted in FIG. 24 where capture member 590 includes two vessel gates are defined by a central member 595 extending from a strut that moves along axis 596 relative to the vessel gate members 594 (also on struts). This strut could also additionally move along the direction of axis 596 and may also have the ability to rotate about the axis 596 (or a different axis aligned with axis 596) to create an opening to act as a vessel gate. Movement of the central member 595 moves the vessel gates to an open position in which openings 599 are provided into the blood vessel apertures 593 found on each side of the central member 595. A blood vessel can enter the blood vessel apertures 593 when the central member 595 is in the open position as seen in FIG. 24. Movement of the central member 595 proximally relative to the gate members 594 closes the openings 599 and captures a blood vessel in one of the blood vessel apertures 593 (it being understood that rather than moving the central member 595 proximally, the central member 594 could be held in the position seen in FIG. 24 while the gate members 594 are advanced distally to close the vessel gates).

With a blood vessel located in one of the blood vessel apertures 593, the stabilizing member 550 can be advanced distally to an extended position such that the blood vessel can be stabilized between the stabilizing member and the gate member 594/central member 595 defining the blood vessel aperture 593. Alternatively, the stabilizing member 550 could be held stationary, while the central member 595 and gate members 594 are moved proximally to stabilize a blood vessel between the stabilizing member 550 and the gate member 594/central member 595 defining the blood vessel aperture 593

In still another variation, opening and closing of one or both of the blood vessel apertures 593 could be accomplished by advancing one or both of the gate members 594 distally along their respective axes 591*a* and 591*b* while the central member 595 is held in a stationary fixed position relative to the inner shaft (not shown). In yet another variation, the central member 595 and one or both of the gate members 594 could be moved in opposite directions such that one moves distally while the other moves proximally to open and close the blood vessel apertures 593.

In the various embodiments described in connection with the structure depicted in FIG. 24, it should be understood that rotational movement of any of the central member 595 and gate members 594 about their respective axes 596, 591*a*, and 591*b* (see, e.g., FIGS. 22B-23D) may be used in conjunction with the translational movement in the distal and/or proximal directions of the various components.

In addition to the various apparatus described herein in connection with FIGS. 16-21, methods of assembling and testing blood vessel harvesting apparatus as described herein may also be provided. The methods may include, for example, positioning at least a portion of an inner shaft 330 within the outer shaft 380; advancing the capture member 390 relative to the inner shaft 330 until the capture member 390 is in its extended position; moving a vessel gate 394 between its open and closed positions; moving a stabilizing member 350 between its refracted position and its extended position when the capture member 390 is in its extended position; rotating the inner shaft 330 and the outer shaft 380 relative to each other about a longitudinal axis 311; and, optionally, advancing a cutting device 364 of a cutting instrument 360 out of the opening of a second lumen 386 in the outer shaft 380.

The shafts of the harvesting apparatus described herein may preferably include one or more lumens in addition to and/or in place of those explicitly described in the embodiments described herein, with the lumens providing passage for, e.g., blood vessel cutting instruments, lights, cameras, fluids, etc.

The various devices, apparatus and components described herein may be constructed of any suitable material and/or combinations of materials known to those skilled in the art.

The complete disclosure of the patents, patent documents, and publications cited herein are incorporated by reference in their entirety as if each were individually incorporated.

Illustrative embodiments are discussed herein and reference has been made to some, but not all, possible variations within the scope of this invention. These and other variations and modifications will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A blood vessel harvesting apparatus comprising:
   an inner shaft comprising a proximal end and a distal end, the inner shaft extending between the proximal end and the distal end;
   an outer shaft comprising a first lumen and a second lumen, wherein at least a portion of the inner shaft is located within the first lumen, and wherein the inner shaft and the outer shaft are configured to rotate relative to each other about a longitudinal axis extending between the proximal end and the distal end of the inner shaft while the inner shaft is located within the first lumen, and further wherein the first lumen and the second lumen each comprise an opening proximate a distal end of the outer shaft;
   a capture member proximate the distal end of the inner shaft, wherein the capture member is operably attached to struts extending through the inner shaft, and wherein the capture member and the struts are movable between a retracted position in which the capture member is located proximate the distal end of the inner shaft and an extended position in which a blood vessel aperture is defined between the distal end of the inner shaft and the capture member, and wherein the capture member comprises a vessel gate that is movable between an open position in which a blood vessel can enter the blood vessel aperture and a closed position in which a blood vessel located in the blood vessel aperture is captured between the capture member and the distal end of the inner shaft, wherein the vessel gate comprises a member that moves distally and/or proximally to move the vessel gate between the open position and the closed position; and
   a stabilizing member located in the blood vessel aperture, wherein the stabilizing member is movable between a retracted position in which the stabilizing member is located proximate the distal end of the inner shaft and an extended position in which the stabilizing member is located proximate the capture member when the capture member is in the extended position, wherein the stabilizing member spans the blood vessel aperture between the distal end of the inner shaft and the capture member, and wherein the stabilizing member is slidably attached to the struts of the capture member such that the stabilizing member slides along the struts when moving between the retracted position and the extended position when the capture member is in the extended position.

2. A blood vessel harvesting apparatus according to claim 1, wherein the inner shaft and the outer shaft rotate 360 degrees about the longitudinal axis relative to each other.

3. A blood vessel harvesting apparatus according to claim 1, wherein the opening of the second lumen is in a fixed position relative to the opening of the first lumen.

4. A blood vessel harvesting apparatus according to claim 1, wherein the vessel gate comprises a rotating member that rotates between the open position and the closed position.

5. A blood vessel harvesting apparatus according to claim 1, wherein the apparatus comprises a cutting instrument comprising a cutting device located at a distal end of a delivery body, wherein at least a portion of the cutting instrument is located within the second lumen of the outer shaft, and wherein the cutting device of the cutting instrument is movable from a retracted position in which the cutting device is located within the second lumen of the outer shaft and an extended position in which the cutting device is located outside of the second lumen proximate the blood vessel aperture.

6. A blood vessel harvesting apparatus according to claim 1, wherein the distal end of the inner shaft comprises a capture member slot, wherein the capture member is located at least partially within the capture member slot when the capture member is in the retracted position.

7. A blood vessel harvesting apparatus according to claim 1, wherein the inner shaft comprises an endoscope lumen that comprises an opening at the distal end of the inner shaft.

8. A method of assembling and testing a blood vessel harvesting apparatus according to claim 1, the method comprising:
- positioning at least a portion of the inner shaft within the outer shaft;
- advancing the capture member relative to the inner shaft until the capture member is in the extended position;
- moving the vessel gate between the open and closed positions;
- moving the stabilizing member between the retracted position and the extended position when the capture member is in the extended position; and
- rotating the inner shaft and the outer shaft relative to each other about the longitudinal axis.

9. A blood vessel harvesting apparatus comprising:
- an inner shaft comprising a proximal end and a distal end, the inner shaft extending between the proximal end and the distal end;
- an outer shaft comprising a first lumen and a second lumen, wherein at least a portion of the inner shaft is located within the first lumen, and wherein the inner shaft and the outer shaft are configured to rotate relative to each other about a longitudinal axis extending between the proximal end and the distal end of the inner shaft while the inner shaft is located within the first lumen, and further wherein the first lumen and the second lumen each comprise an opening proximate a distal end of the outer shaft;
- a capture member proximate the distal end of the inner shaft, wherein the capture member is operably attached to struts extending through the inner shaft, and wherein the capture member and the struts are movable between a retracted position in which the capture member is located proximate the distal end of the inner shaft and an extended position in which a blood vessel aperture is defined between the distal end of the inner shaft and the capture member, and wherein the capture member comprises two vessel gates, wherein each vessel gate is movable between an open position in which a blood vessel can enter the blood vessel aperture and a closed position in which a blood vessel located in the blood vessel aperture is captured between the capture member and the distal end of the inner shaft, and wherein each vessel gate comprises a separate rotating member such that each vessel gate can be moved between the open and closed positions independently of the other vessel gate; and
- a stabilizing member located in the blood vessel aperture, wherein the stabilizing member is movable between a retracted position in which the stabilizing member is located proximate the distal end of the inner shaft and an extended position in which the stabilizing member is located proximate the capture member when the capture member is in the extended position, wherein the stabilizing member spans the blood vessel aperture between the distal end of the inner shaft and the capture member, and wherein the stabilizing member is slidably attached to the struts of the capture member such that the stabilizing member slides along the struts when moving between the retracted position and the extended position when the capture member is in the extended position.

10. A blood vessel harvesting apparatus according to claim 9, wherein the inner shaft and the outer shaft rotate 360 degrees about the longitudinal axis relative to each other.

11. A blood vessel harvesting apparatus according to claim 9, wherein the opening of the second lumen is in a fixed position relative to the opening of the first lumen.

12. A blood vessel harvesting apparatus according to claim 9, wherein the apparatus comprises a cutting instrument comprising a cutting device located at the distal end of a delivery body, wherein at least a portion of the cutting instrument is located within the second lumen of the outer shaft, and wherein the cutting device of the cutting instrument is movable from a retracted position in which the cutting device is located within the second lumen of the outer shaft and an extended position in which the cutting device is located outside of the second lumen proximate the blood vessel aperture.

13. A blood vessel harvesting apparatus according to claim 9, wherein the distal end of the inner shaft comprises a capture member slot, wherein the capture member is located at least partially within the capture member slot when the capture member is in the retracted position.

14. A blood vessel harvesting apparatus comprising:
- an inner shaft comprising a proximal end and a distal end, the inner shaft extending between the proximal end and the distal end;
- an outer shaft comprising a first lumen and a second lumen, wherein at least a portion of the inner shaft is located within the first lumen, and wherein the inner shaft and the outer shaft are configured to rotate relative to each other about a longitudinal axis extending between the proximal end and the distal end of the inner shaft while the inner shaft is located within the first lumen, and further wherein the first lumen and the second lumen each comprise an opening proximate a distal end of the outer shaft;
- a capture member proximate the distal end of the inner shaft, wherein the capture member is operably attached to struts extending through the inner shaft, and wherein the capture member and the struts are movable between a retracted position in which the capture member is located proximate the distal end of the inner shaft and an extended position in which a blood vessel aperture is defined between the distal end of the inner shaft and the capture member, and wherein the capture member comprises two vessel gates, wherein each vessel gate is movable between an open position in which a blood vessel can enter the blood vessel aperture and a closed position in which a blood vessel located in the blood vessel aperture is captured between the capture member and the distal end of the inner shaft; and wherein the capture member comprises a common rotating member, wherein rotation of the common rotating member moves both of the vessel gates between the open and closed positions; and
- a stabilizing member located in the blood vessel aperture, wherein the stabilizing member is movable between a retracted position in which the stabilizing member is located proximate the distal end of the inner shaft and an extended position in which the stabilizing member is located proximate the capture member when the capture member is in the extended position, wherein the stabilizing member spans the blood vessel aperture between the distal end of the inner shaft and the capture member, and wherein the stabilizing member is slidably attached to the struts of the capture member such that the stabilizing member slides along the struts when moving between the retracted position and the extended position when the capture member is in the extended position.

15. A blood vessel harvesting apparatus according to claim 14, wherein the inner shaft and the outer shaft rotate 360 degrees about the longitudinal axis relative to each other.

16. A blood vessel harvesting apparatus according to claim 14, wherein the opening of the second lumen is in a fixed position relative to the opening of the first lumen.

17. A blood vessel harvesting apparatus according to claim 14, wherein each vessel gate comprises a member that moves distally and/or proximally to move the vessel gate between the open position and the closed position.

18. A blood vessel harvesting apparatus according to claim 14, wherein the apparatus comprises a cutting instrument comprising a cutting device located at a distal end of a delivery body, wherein at least a portion of the cutting instrument is located within the second lumen of the outer shaft, and wherein the cutting device of the cutting instrument is movable from a retracted position in which the cutting device is located within the second lumen of the outer shaft and an extended position in which the cutting device is located outside of the second lumen proximate the blood vessel aperture.

19. A blood vessel harvesting apparatus comprising:
an inner shaft comprising a proximal end and a distal end, the inner shaft extending between the proximal end and the distal end;
an outer shaft comprising a first lumen and a second lumen, wherein at least a portion of the inner shaft is located within the first lumen, and wherein the inner shaft and the outer shaft are configured to rotate relative to each other about a longitudinal axis extending between the proximal end and the distal end of the inner shaft while the inner shaft is located within the first lumen, and further wherein the first lumen and the second lumen each comprise an opening proximate a distal end of the outer shaft;
a capture member proximate the distal end of the inner shaft, wherein the capture member is operably attached to struts extending through the inner shaft, and wherein the capture member and the struts are movable between a retracted position in which the capture member is located proximate the distal end of the inner shaft and an extended position in which a blood vessel aperture is defined between the distal end of the inner shaft and the capture member, and wherein the capture member comprises two vessel gates, wherein each vessel gate is movable between an open position in which a blood vessel can enter the blood vessel aperture and a closed position in which a blood vessel located in the blood vessel aperture is captured between the capture member and the distal end of the inner shaft, and wherein each vessel gate comprises a member that moves distally and/or proximally to move the vessel gate between the open position and the closed position; and
a stabilizing member located in the blood vessel aperture, wherein the stabilizing member is movable between a retracted position in which the stabilizing member is located proximate the distal end of the inner shaft and an extended position in which the stabilizing member is located proximate the capture member when the capture member is in the extended position, wherein the stabilizing member spans the blood vessel aperture between the distal end of the inner shaft and the capture member, and wherein the stabilizing member is slidably attached to the struts of the capture member such that the stabilizing member slides along the struts when moving between the retracted position and the extended position when the capture member is in the extended position.

20. A blood vessel harvesting apparatus according to claim 19, wherein the inner shaft and the outer shaft rotate 360 degrees about the longitudinal axis relative to each other.

21. A blood vessel harvesting apparatus according to claim 19, wherein the opening of the second lumen is in a fixed position relative to the opening of the first lumen.

22. A blood vessel harvesting apparatus according to claim 19, wherein the apparatus comprises a cutting instrument comprising a cutting device located at a distal end of a delivery body, wherein at least a portion of the cutting instrument is located within the second lumen of the outer shaft, and wherein the cutting device of the cutting instrument is movable from a retracted position in which the cutting device is located within the second lumen of the outer shaft and an extended position in which the cutting device is located outside of the second lumen proximate the blood vessel aperture.

23. A blood vessel harvesting apparatus according to claim 19, wherein the distal end of the inner shaft comprises a capture member slot, wherein the capture member is located at least partially within the capture member slot when the capture member is in the retracted position.

* * * * *